United States Patent [19]
Chiang et al.

[11] Patent Number: 5,821,057
[45] Date of Patent: Oct. 13, 1998

[54] ASSAY FOR AGENTS THAT AFFECT CHOLESTEROL 7ALPHA-HYDROXYLASE EXPRESSION AND A CHARACTERIZATION OF ITS REGULATORY ELEMENTS

[75] Inventors: John Y. L. Chiang, Stow; Diane Stroup, Alliance, both of Ohio

[73] Assignee: Northeastern Ohio Universities, Rootstown, Ohio

[21] Appl. No.: 562,985

[22] Filed: Nov. 27, 1995

[51] Int. Cl.$^6$ .............................. C12Q 1/68; C12N 5/10; C12N 15/11
[52] U.S. Cl. .............................. 435/6; 435/370; 536/23.1
[58] Field of Search ........................... 435/6, 320.1, 325, 435/370; 536/23.1, 23.2, 23.5, 24.1

[56] References Cited

FOREIGN PATENT DOCUMENTS

| | | |
|---|---|---|
| 648 840 A | 4/1995 | European Pat. Off. . |
| 648 841 A | 4/1995 | European Pat. Off. . |
| 91/15213 | 10/1991 | WIPO . |
| 92/13063 | 8/1992 | WIPO . |
| 92/18523 | 10/1992 | WIPO . |
| 94/18346 | 8/1994 | WIPO . |

OTHER PUBLICATIONS

Y. Li et al., "The Expression of a Catalytically Active Cholesterol 7α–Hydroxylase Cytochrome P450 in *Escherichia coli*", The Journal of Biological Chemistry, vol. 266, No. 29, Oct. (1991) 19186–19191.
M. Noshiro et al., "Molecular cloning of cDNA for Cholesterol 7α–Hydroxylase from Rat Liver Microsomes", FEB, vol. 257, No. 1, Oct. (1989), pp. 97–100.
D. P. Wang et al., "Structure and Nucleotide Sequences of the Human Cholesterol 7α–Hydroxylase Gene (CYP7)", Genomics, vol. 20, Nov. (1994), pp. 320–323.
Database WPI, AN 92–214120, JP 04 144 680, May (1992).
Hoekman et al. "Transcriptional regulation of the gene encoding cholesterol 7α–hydroxylase in the rat", *Gene* 130: 217–223 (1993).
Lee et al., "Multiple Functional DBP Sites on the Promoter of the Cholesterol 7α–hydroxylase P450 Gene" *J. Biol. Chem.* 269(20): 14681–14689n (May 10, 1994).
Cooper et al. "Characterization of Hepatic–specific Regulatory Elements in the Promoter Region of the Human Cholesterol 7–alpha–hydroxylase Gene", *J. Biol. Chem.* 272(6): 3444–3452 (Feb. 7, 1997).
Wang et al. "Transcriptional Regulation of the Human Cholesterol 7 alpha–hydroxylase Gene (CYP7A) In HEPG2 Cells", *J. Lipid Research* 37(9): 1831–8141 (1996).
Karam, W. G. et al., "Polymorphisms of Human Cholesterol 7α–Hydroxylase", *Biochem. and Biophys. Res. Comm.* 185(2): 588–595 (1992).
Breslow, J. L. et al., "Transgenic Mouse Models of Lipoprotein Metabolism and Atherosclerosis", *Proc. Natl. Acad. Sci. USA* 90: 8314–8318 (1993).
Cohen, J. C. et al., "Cloning of the Human Cholesterol 7α–Hydroxylase Gene (CYP7) and Localization to Chromosome 8q11–q12", *Genomics* 14: 153–161 (1992).
Nishimoto, M. et al., "Structure of the Gene Encoding Human Liver Cholesterol 7α–Hydroxylase", *Biochimica. et Biophysica. Acta.* 1172: 147–150 (1993).
Thompson, J. F. et al., "Cholesterol 7α–Hydroxylase Promoter Separated from Cyclophilin Pseudogene By Alu Sequence", *Biochimica et Biophysica Acta* 1168: 239–242 (1993).
Molowa, D. T. et al., "Transcriptional Regulation of the Human Cholesterol 7α–Hydroxylase Gene", *Biochemistry* 31: 2539–2544 (1992).
Nishimoto, M. et al., "Structural Analysis of the Gene Encoding Rat Cholesterol α–Hydroxylase, The Key Enzyme for Bile Acid Biosynthesis", *The Journal of Biological Chemistry* 266(10): 6467–6471 (1991).
Jelinek, D. F. et al., "Structure of the Rat Gene Encoding Cholesterol 7α–Hydroxylase", *Biochemistry* 29(34): 7781–7785 (1990).
Chiang, J. Y. L. et al., "Cloning and 5'Flanking Sequence of a Rat Cholesterol 7α–Hydroxylase", *Biochimica et Biophysica Acta* 1132: 337–339 (1992).
Crestani et al. "Genomic Cloning, Sequencing, and Analysis of the Hamster Cholesterol 7α–Hydroxylase Gene (CYP7)", *Archives of Biochem. and Biophys.*, 306(2): 451–460 (1993).
Lusis, Aldons J., "The Mouse Model for Atherosclerosis", *TCM* 3(4): 135–143 (1993).
Dueland, Sveinn et al., "Effect of Dietary Cholesterol and Taurocholate on Cholesterol 7α–hydroxylase and Hepatic LDL Receptors in Inbred Mice", *Journal of Lipid Research* 34: 923–931 (1993).
Dueland, Svein et al., "Expression of 7α–Hydroxylase in Non–hepatic Cell Results in Liver Phenotypic Resistance of the Low Density Lipoprotein Receptor to Cholesterol Repression", *Journal of Biological Chemistry* 267(32): 22695–22698 (1992).
Ness, et al. "Effect of Thyroid Hormone on Hepatic Cholesterol 7α–Hydroxylase, LDL Receptor, HGM–CoA Reductase, Farnesyl Pyrophosphate Synthetase and Apolipoprotein A–I mRNA Levels in Hypophysectomized Rats", *Biochem. and Biophys. Res. Comm.*, 172(3):1150–1156 (1990).
Ciliberto, et al."Inducible and Tissue–specific Expression of Human C–reative Protein in Transgenic Mice", *EMBO Jour.* 6: 4017–4022 (1987).
Gordon, J.W. et al."Integration and Stable Germ Line Transmission of Genes Injected into Mouse Pronuclei", *Science* 214:1244–1246 (1981).

(List continued on next page.)

*Primary Examiner*—Nancy Degen
*Assistant Examiner*—Robert Schwartzman
*Attorney, Agent, or Firm*—Foley & Lardner

[57] ABSTRACT

DNA regulatory elements that control cholesterol 7α-hydroxylase (CYP7) expression are disclosed, including a CYP7 minigene that comprises nucleotides downstream from about −371 of the proximal promoter region through about the middle of intron II, inclusive of intron I. This minigene further is stably transfected into a cell line, along with a reporter gene. A method is provided for screening agents that inhibit or stimulate expression of the minigene.

19 Claims, 24 Drawing Sheets

OTHER PUBLICATIONS

Brinster, R.L. et al."Introns Increase Transcriptional Efficiency in Transgenic Mice", *Proc. Natl. Acad. Sci.* 85:836–840 (1988).

Crestani, et al."Molecular Cloning of the Hamster Gene Encoding Cholesterol 7α–Hydroxylase", *FASEB Jour.* V6(4), A2626 (1992) Abstract.

Sambrook et al."Molecular Cloning . . . ", *A Laboratory Manual* pp. 15.3–15.4, 15.14–15.19, 15.32–15.36, 15.51–15.52. CSH Lab. Press. N.Y. (1989).

Wasylyk, B. "Enhancers and Transcription Factors in the Control of Gene Expression", *Biochem. Biophys. ACTA* 951, 17–35 (1988).

Hylemon et al."Hormonal Regulation of Cholesterol 7α–Hydroxylase mRNA Levels and Transcriptional Activity in Primary Rat Hepatocyte Cultures", *J. Biol. Chem.* 267 (24), 16866–16871 (1992).

Pandak et al."Regulation of Cholesterol 7α–Hydroxylase mRNA and Transcriptional Activity by Taurocholate and Cholesterol in the Chronic Biliary Diverted Rat", *J. Biol. Chem.* 266(6) 3416–3421 (1991).

Pandak et al."Bile Acid Synthesis. VI. Regulation of Cholesterol 7α–Hydroxylase by Taurocholate and Mevalonate", *J. Lipid Res.* 33 659–668 (1992).

Ramirez et al."Cholesterol and Bile Acids Regulate Cholesterol 7α–Hydroxylase Expression at the Transcriptional Level in Culture and in Transgenic Mice", *Mol. Cell. Biol.* 14(4) 2809–2821 (1994).

Noshiro et al."Molecular Cloning and Sequence Analysis of cDNA Encoding Human Cholesterol 7α–Hydroxylase", Febs Lett 268(1), 137–140 (1990).

Sambrook et al."Molecular Cloning: A Laboratory Manual" 2nd ed; Cold Spring Harbour Laboratory Press, Cold Spring Harbor, 1989, 16.1–16.72 & 17.1–17.41.

Ausubel et al. Short Protocols in Molecular Biology, 2nd ed: (John Wiley & Sons, New York), pp. 9.17 to 9.23.

Lai et al."Transcriptional Control in Hepatocytes: a Window on Development", TIBS 16, 427–430 (1991).

Crestani, et al."Hormonal Regulation of the Cholesterol 7α Hydroxylase gene (CYP7)," *J. of Lipid Research* 36: 2419–2432 (1995).

Chiang, et al."Identification and Characterization of a Putative Bile Acid–responsive Element in Cholesterol 7α–Hydroxylase Gene Promoter," *J. of Biological Chemistry* 269(26): 17502–17507 (1994).

Karam, et al."Expression and Purification of Human Cholesterol 7α–Hydroxylase in *Eschericia coli*", *J. of Lipid Research* 35: 1222–1231 (1994).

Crestani, et al."Effects of Bile Acids and Steroid/Thyroid Hormones on the Expression of Cholesterol 7α mRNA and the CYP7 Gene in HepG2 Cells," *Biochemical and Biophysical Research Communications* 198(2): 546–553 (1994).

Chiang, et al."Regulation of Cholesterol 7α–Hydroxylase in the Liver," *J. of Biological Chemistry* 285(7): 3889–3897 (1990).

Pandak, et al."Failure of Intravenous Infusion of Taurocholate to Down–Regulate Cholesterol 7α–Hydroxylase in Rats With Biliary Fistulas," *Gastroenterology* 108: 533–544 (1995).

Vlahcevic, et al."Hepatic Cholesterol Metabolism," *The Liver Biology and Pathobiology,* Third Edition 22: 379–389 (1994).

Jones, et al."Cholesterol 7αHydroxylase: Evidence for transcriptional regulation by Cholesterol or Metabolic products of Cholesterol in the Rat," *J. of Lipid Research* 34: 885–892 (1993).

Chiang, et al."Reversed Phase High–Performance Liquid Chromatography Assay of Cholesterol 7α–Hydroxylase," *Methods in Enzymology* 206(46) 483–489 (1991).

Li, et al."Regulation of Cholesterol 7α–Hydroxylase in the Liver," *J. of Biological Chemistry* 265(20): 12012–12019 (1990).

Pandak, et al."Expression of Cholesterol 7α–Hydroxylase In Response to Cholesterol and Bile Acid Feeding In The Hamster and Rat," *Gastroenterology* 108 (1995) Astract A1141.

Stroup, et al."The Bile Repression of Cholesterol 7α–Hydroxylase Gene Transcription May Be Mediated Through Multiple Elements In The Promoter," *Advances In Gene Technology: Protein Engineering and Structural Biology* p. 76 (1995)Abstract.

Jones, et al."Regulation Of Rat Cholesterol 7α–Hydroxylase (C7αH) MASS mRNA and Transcriptional Activity By Cholesterol," AGA AGA Annual Meeting (1991) Abstract A757.

Breuer, et al."Cholesterol 7α–Hydroxylase Is Up–Regulated By The Competitive Inhibitor 7–Oxocholesterol In Rat Liver," *Eur. J. Biochem* 215 pp. 705–710 (1993).

Pandak, et al."Regulation Of Cholesterol 7α–Hydroxylase m–RNA And Transcriptional Activity By Taurocholate (TCA) In The Chronic Bile Fistula (CBF) Rat," *Hepatology* 12(4) p. 873 (1990) Abstract A 141.

Chiang, et al."The Cholesterol 7α–Hydroxylase Gene Promoter Contains A Novel Negative Regulatory Element and Regions Conferring Regulation By Bile Acids, Dexamethasone, Insulin, cAMP, Phorbol Esters, Retinoic Acid, and Coup–TFI," *Liver Gene Development, Gene Regulation and Disease* p. 63, France (1995) Abstract.

Pandak, et al. "Intraduodenal (ID), But Not Intravenous (IV) Infusion of Taurocholate (TCA) Down–Regulates HMG–CoA Reductase: (HMG–CoA–R) and Cholesterol 7α–Hydroxylase (C7aH)," *Gastroenterology* 106(4) Part 2 (1994) Abstract.

Stroup, et al."Identification Of A Negative Regulatory Element In The Cholesterol 7α–Hydroxylase Gene (CYP7) Proximal Promoter," *II Drug Affecting Lipid Metabolism* Houston (1995) p. 48 Abstract.

Crestani, et al."Characterization Of The Rat Cholesterol 7α–Hydroxylase Gene (CYP7) Promoter," Drugs affecting Lipid Metabolism Houston (1995) p. 123 Abstract.

Stroup, et al."The Bile Acid Responsive Elements if Located In The Proximal Promoter Of The Cholesterol 7α–Hydroxylase Gene (CYP7)," *FASEB J.* 8 A1250 Abstract X59.

Wang et, al."Transcriptional Regulation Of Human Cholesterol 7α–Hyadroxylase Gene in HepG2 Cells," *FASEB J.* 8:A1383 (1994) Abstract 724.

Crestani, et al."Transcriptional Regulation Of The Cholesterol 7α–Hydroxylase Gene (CYP7) By Multiple Factors," *FASEB J.* 9:A1334 (1995) Abstract 453.

Chiang, et al."Expression And Purification Of A Catalytically Active Cholesterol 7α–Hydroxylase In *E. Coli*," 15th Int'l Congress of Biochem Jeruslem Israel (1991) p. 35 Abstract.

Pandak, et al."Expression Of Cholesterol 7α–Hydroxylase In Response to Cholesterol And Bile Acid Feeding In The Hamster And Rat," Gastroenterology 108, A1141 (1995) Abstract.

Jones, et al. "Effects Of Extrahepatic Cholestasis (EHC) On Four Rate–Limiting Enzymes Of Hepatic Cholesterol (XOL) Metabolism," Gastroenterology 102(4) Pt 2 PA 828 (1992) Abstract.

Crestani, et al. "Molecular Cloning Of The Hamster Gene Encoding Cholesterol 7α–Hydroxylase," *FASEB J.* 6:A1389 (1992) Abstract P2626.

Vernell, et al. "Transgenic Mice Carrying Rat Cholesterol 7α–Hydroxylase," *FASEB J.* 5: 11344 (1991) Abstract 2360.

Li, et al. "Expression Of Catlytically Active Cholesterol 7α–Hydroxylase In *E. Coli*," *FASEB J.* 5: A1164 (1991) Abstract 4597.

Li, et al. "Cloning, Sequencing and Regulation of Cholesterol 7-60 –Hydroxylase," *FASEB J.* 4: A2241 (1990) Abstract 3162.

Chiang, et al. "Identification Of A Liver Nuclear Protein Factor Responsive To The Repression Of Cholesterol 7α–Hydroxylase Gene By Bile Acids," *FASEB J.* 8: A543 (1994) Abstract 3149.

Qiu, et al. "Regulation Of Cholesterol 7α–Hydroxylase By Female Sex Steroids," *FASEB J.* 8: A 959 (1994) Abstract 5553.

Crestani, et al. "Cloning And Sequencing Of The Hamster Cholesterol 7α–Hydroxylase Gene (CYP7) And A Comparative Analysis Of The Rat, Hamster and Human CYP7 Genes," *FASEB J.* A1126 (1993) Abstract 1013.

Pandak, et al. "Hormonal Regulation Of Cholesterol 7α–Hydroxylase (C7αaH) Specific Activity, mRNA Levels And Transcriptional Activity," *Hepatology* 18: 179A (1993) Abstract 491.

Pandak, et al. "Failure Of Mevalonate To Prevent Down–Regulation Of Cholesterol 7α–Hydroxylase By Taurocholate Infusion In Chronic Billiary Diverted Rats," Hepatology 14: 258A (1991) Abstract 842.

Stroup, et al. "Identification Of A Negative Regulatory Element In The Cholesterol 7α–Hydroxylase Gene (CYP7) Proximal Promoter," *FASEB J.* 9: A1334 (1995) Abstract 452.

FIG. IA

```
-2235   TTTTGGTTATCTTTCAGCCGTGCCCCACTCTACTGGTACCAGTTACTGTATTAGTCGATTTTCATGCTGCTGATAAAGACATACCTG

-2145   AAACTGGACAATTACAAAAGAAAGAGTTTATTGGACTTACACATTCTACATCACTTGGGAGCCCTCACAATCATGATGAAGGAGAAAGGC

-2053   ACATCTCACATGGCAGCAGACAAGAAAAGAGCTTGTGCAGGGAAACTCCTCTTTTAAAACCATCAGATCTCATGAATTATTCATTATCA

-1961   TGACAATAGCCACAGGAAAGAACTGCACCCATAATTCAGTCACCTCCTCCCACAACACGTGAGAATTCAAGATGAGATTGG
                                                                              GRE
-1869   ATGGGGACACAGCCAAACCATGTCACACTACCAGCCAAACCATGTCCTTCCATTTTGTATATTGCTGTTCTTCATTGCCCGAGAAGTAA
                        C/EBP NFI/CTF
-1777   CTCTAAAGGGCTGTATATTTGGATATTAGATTGGCATTTTATCTGACTGGGATATCTTGCTGTGCCATGTATAAGATCAGCTTTTC
                                                                           HNF4
-1685   TATAAGCCCATATTTTTAAAAGATATATTAATTTTTTAAAAATCCACCTGTCTAAATAAATGCACAAAGCCCCCCAAAAACCTAGATTCTAA

-1593   GAAAAATCTATGTCACTGCCATACACAATGATTGATATTAATTATGGTGATAATTACACACAAAAATGTGATCTCTGTTTAAACAGGC
                                                       NFI/CTF
-1501   AAAAACAAAAAAACACATGAAATAAATCTATGGCATCTATAGCCAAAACTGAAACAACCCACATATCCATCAATAGGAAATCAGTTAAATAA
                                                               GRE
-1409   ATTATAGTACATTTAT[CCAAT]GGAAGATTAAGCACACATATTCAATATAATATATACACACAGTACTGTTGCCTACCTCTTTTGTCTTAATTCTGTGAAC
                                                                                                   ARP1 AP1
-1317   AATACTGTGGGTGTATGTGTGTGTTTATATACACATATATACACTTTTTGGTTCTTAGACTCACCAAGTTGATCCTTGACTCAAGACATTGCATTTGCTGC

-1225   TCTCATTCACTCTGCTTCAGTAGGATACCCTCCTTCTGATATTCACATGAGTAGTCTCTTCTGTCATTCAGATCTCAAATGTCACAATTTCAGAGAGCCC

-1133   TTCCCTCTTCCTGAATATCATCTAAAGTTGTCCCTCATTCCCCCATAGGAAATCTGCCTATCTTATTAATGCCTGCAACTGGAATACTTTGAAGAGTTCTTGGCA

-1041   ATCTCTGATCATCATATCTAAAGTTGTCCCTCATTCCCCCATAGGAAATCTGCCTATCTTATTAATGCCTGCAACTGGAATACTTTGAAGAGTTCTTGGCA

-949    TTTCTCCATTGGAATAGAATCTCAACTAATATTTTGTGTACACAGAAATAAAGTTTGGAAGACAGATGCCAAATTGTTACTAGTGGTTACTTCTGAGTA
                                                           GRE              HNF1        HNF1
-857    CGTAATAAATACTCAACTAATATTTTGTGTACACAGAAATAAAGTTTGGAAGACAGATGCCAAATTGTTACTAGTGGTTACTTCTGAGTA
                                                           GRE              HNF1        HNF1
-765    AAGGAGTAGCATGGTAGGTAAAATTATTAATAGATGTTCACTTTCCACCAAGATATGTTTTAGTTAGTCTTAACTTACTTGAAATGAAATTTA
                                                                                HNF1
```

FIG. 1B

```
-673  TTACTTTAATAATTAGAAACATTTGATAAACATTTAGTCACAAGAATGATAGATAAAATTTGATGCTTCCAATAAGTTATATTTATCTAGA
                                                                            HNF I
-581  GGATGCACTTATGTAGAATACTCTCTTGAGGATGTTAGGTGTAACATGTTACTATATGTAGTAACATCTATGATTTTATAAAAGCACT
-489  GAAACATGAAGCAGCAGAAATGTTTTTCCCAGTTCTCTCTTCCTCTGAACTGTCTCTGGCAAAGCACCTAAATTAATTCTTCT
-397  TTAAAAGTTAACAAGACCAAATTATAAGCTTGATGAATAACTCATTCTTATCTTTCTTTAAATGATTATAGTTTATGTATTATTAGCTATG
                    GRE                                                          DBP
-305  CCCATCTTAAACACAGGTTTATTTGTTCTTTTTTACACATACCAAACTCTTAATATTAGCTGTGTTGTCCCCAGTCCGAATGTTAAGTCAACATAT
                                                                              HNF 4   TRE    HNF I
-213  ATTTGAGAGACCCTTCAACTTATCAAGTATTGCAGGTCTCAGTTCGCTTTGGAACCACTTCTGATACCTGTGGACTTAGTTCAAGCCAGTTA
              NFI   TGT3/HNF3  HRE          HNF I
-121  CTACCACTTTTTTTTTTTCTAATAGAATGAACAAATGGCTAATTGTTGCTTTGTCAACCAAGCTCAAGTTAATGGATCTGGATACTATGTAT
                                        *                        1     2    3
-29   ATAAAAAGCCTAGCTTGAGTCTCTCTTTCAGTGGCATCCTCCCTTTCTAATCAGAGATTTCTTCCTCCAGAGATTTGGCCTAGATTTGCAA
  1                                                                                               Exon
       Met Met Thr Ser Leu Ile Trp Gly Ile Ala Ile Ala Ala Sys Sys Sys Leu Trp Leu Ile Leu
 64   A ATG ATG ACC TCA CTT TTG ATT TGG GGG ATT GCT ATA GCA GCA TGC TGT TGT CTA TGG CTT ATT CTT
       Gly Ile Arg Arg Arg
 23
131   GGA ATT AGG AGA AGG TAAGTAATGTTTTATCTTTAAATGCTCTCTTTGATTCATCCATTAATTTTTTACCTTCATTTTATACAGT
218   AAATTTGGTTTTCTATACTTACACATATTAGCATTATATCTTCCTTATGTTTAAATGAAAAATTGATTGAATTTTAAAGTAATATCTTTT
310   TTACTATATCTCACAAGACATATGACAGCTTCCCCTTTTAGTATTGGCATATAAATGTAATATAAATGTATATTGGTGTTAAACATA
402   ACTGACAGAAATTGTATAAGGTCTCTATGTACATTTATATGTATCTAAAGAGGAAGCCCAGATTAGTAAGGATACAAGTAGCAAGTGGGA
                                                                                      GRE
494   ATCTACAATGGAAAGGATTGCTTTCTCTCACATGGCTTCAATAGATACTCTTGCTTAAATAAATGTTCTCTTTAAGCTCATTCTTGTGCAT
                                                                                    HNF I    Intron
586   CGCATAGACTCAGCCTAGCCTGAACAAGAGACATAGAGCCTGAGCTCGATCATTCTATTACTGTTTTAAATAAATGTTAATCAACTGGTG
678   AATTGGGAAAGTTTGCTTGAGTGTATGTGACATCGATTTCATTTATTTACAACTGGTTCAAGAATGCAAGAAAACAAATACAGTCAGATCCA
770   GAACCATAGTTTATTAACTTCTAAATTGGCTCAAGGAGTAATTGTGGGGAGGCATATAGATAATTCTCTGCTATGTCAATCTCAATCTCAAAAAGAGAA
```

FIG. 1C

```
 862 AATAACCCTAACCATCTTCAGCTTTGTAGATTGCTATGTGTTTCTGCCTTTGCAGTTTCTTTCGCAGTTTCTTTCAGGCCTGATAGTTTTTACTTTTAATTA
 954 AACTACTTATCTTCAAACTAAGAAAAGAAAAGTAATTACTTTATACTTTATATTCTAATCAAGAGAGTACAGAAGTTTATGTTGGAAAATAAG
                                                                              EBP
1046 TTTACATGTTCTAATAAAAACATTTTAAAGGAGCACTGAATTACAATAGATGATTCCGTCAGTGTTTACTTACTCAATTCATTTTATAAT
1138 AAGCTGATTCTCTCACATGAGATTCTTCTCTCTCGAAACCATCCTTATAGAATAATATAGATATCTTAAACTAGGAATATTTCAAAACC
1230 TCAGTTCTGAAATCCCCTCCCTTATTCAGTGATCTGTCTTTAAAGAAAATAATCAAAAGAACATTTGAGATATTTAGAAAAATGATGCTT
1322 AGCAAAGTGATAAACACTAGAAGTAGTTTTGTTTCCGCACTGACAACAAGAATCTGTTGGTCTTGTAAATCCTTTGCCTGTATCACTGG
1414 GAAAAGTGATGAGCACATAGACGGGTGCTTGTTGAATGTATATGGACGATGCATGAATGGATTAGTAATCCTATAAACTATAGGGTTTC
1506 CATATCATGTTACTAGGTTAATATAACCTATTACTGTAGTAAGTAAGTAAAAACCCAACAAAGAATATCTATAAACTATACACTGTGTCTG
     HNF I
1598 AAAGTTTGAAGTCAGTGGGAAAATTTTAAAACCTGATGTAAGTAAAAACCCAAAACTGTAATCATCCATGTCTATCATACACTGTGTCTG
                                              Xba I
  28                                     Leu|Glu Asn Gly Leu Ile Pro Tyr Leu Gly Cys Ala Leu Gln Phe
1690 ACAGG Gln Thr Gly Glu Pro Pro CTA GAG AAT GGA TTA ATT CCA TAC CTG GGC TGT GCT CTG CAA TTT
     CAA ACG GGT GAA CCA CCT
                                                                                    Exon II
  49 Gly Ala Asn Pro Leu Glu Phe Leu Arg Ala Asn Gln Arg Lys His Gly Val Phe Thr Cys Lys Leu
1758 GGT GCC AAT CCT CTT GAG TTC CTC AGA GCA AAT CAA AGG AAA CAT GGT GTT TTT ACC TGC AAA CTA
  72 Met Gly Lys Tyr Val His Phe Ile Thr Asn Pro Leu Ser Tyr His Lys Val Leu Cys His Gly Lys Tyr
1827 ATG GGA AAA TAT GTC CAT TTC CAT ATC ACA AAT CCC TTG TCA TAC CAT AAG GTG TTG TGC CAC GGA AAA TAT
  95 Phe Asp Trp Lys Phe His Phe Ala Thr Ser Ala Lys
1896 TTT GAT TGG AAA TTT CAC TTTT GCT ACT TCT GCG AAG GTAAGCAGTTTTACATTTATATACCATTCTGTTTGTCTTC
1975 TACCTTTTTATGTGCTTGTCTATTAGAAATTTGATGTACTTAGATTTTATGATAAAGGTGTTGAAGAGAGTTATCCTTATGTGGAGATTC
2067 TTAGAAACATAAATAAATTATACGTAGCTTCTGTAGTAATAATCATTTAGAAAGTCAAAATAGGTATAGATTCCGTCATTTGCTTTGCACGA
```

FIG. ID

```
2159 GCTAATGAGGGTGAAATACAGATTAAATGCTCTACTGAGACAGTGGCACTGTACGAATAAGATAGATTAAAATTCATCACATCAGCAATGT
                                                                      SRE
2251 CTATGCAGAGCGAAGTGACGGAAACCTAACATTCAGCAGTGTCTCACCACACTGTGCCACACAGTGTTTCATTTGATAAGGAATTGGCA
                                          BglII    HNFI
2343 AGATATTTAACATCATTAGATGTAATAAAGAAGATCTGTTACTGAGAAAAAAACCAATAACTACTTACTGCAAATAAATATTAG
2435 CTTTGGTCTTTGTGACTAAGTAGTTAAAGTTTGGTTAAAATACATCTACAGCTGGACACACCTGAACACACCTGAGTCCCTGCTATTTGA
2527 GAGGCTGAGGCAGGAGGATCGCTTGAGTCCAGGAGTTTGAGGCTGCAGTGAGCTATCATTGTGTCACTGCACTCCAGCCTGGGTGACAATGT
2619 GAGACCCCATCTCTAAAAGAAAAGAAAATCTACAAATATATAAAGATAACTAAATATTTAAACATTATCAATTAGTTTATGT
2711 GCAATAGCTGTAAATAAGTGCAGTAGCATAAGAAATAAGACATAGAGAAATAAAGACTTGAGTGATCCAGGGAGTGCCACTGAGTTGGCTTTAAAGG
2803 AAAGGTACAGTTTGGTCATTTATTGTAAAGTGCTATGAACTTGTACAAGGGAAAGCCAATTCCCGTGTTTACCAAGTAAGAACTATGAA
                                                                                        Ala Phe
108
2895 AGTATCTAATCCGTTTTTCAGTCATTTACTAGTCAGGTTTAACTTCTTTTTCGCATGTTTTATTTGCTATCAG GCA TTT
                    TRE
110 Gly His Arg Ser Ile Asp Pro Met Asp Gly Asn Thr Thr Glu Asn Ile Asn Asp Thr Phe Ile Lys Thr
2982 GGG CAC AGA AGC ATT GAC CCG ATG GAT GGA AAT ACC ACT GAA AAC ATA AAC GAC ACT TTC ATC AAA ACC

133 Leu Gln Gly His Ala Leu Asn Ser Leu Thr Glu Ser Met Met Glu Asn Leu Gln Arg Ile Met Arg Pro
3051 CTG CAG GGC CAT GCC TTG AAT TCC CTC ACG GAA AGC ATG ATG GAA AAC CTC CAA CGT ATC ATG AGA CCT

156 Pro Val Ser Ser Asn Ser Lys Thr Ala Ala Trp Val Thr Glu Gly Met Tyr Ser Pag Cys Tyr Arg Val
3120 CCA GTC TCC TCT AAC TCA AAG ACC GCT GCC TGG GTG ACA GAA GGG ATG TAT TCT TTC TGC TAC CGA GTG
                                                                                            Exon III
179 Met Phe Glu Ala Gly Tyr Leu Thr Ile Phe Gly Arg Asp Leu Thr Arg Arg Asp Thr Arg Gln Lys Ala His
3189 ATG TTT GAA GCT GGG TAT TTA ACT ATC TTT GGC AGA GAT CTT ACA AGG CGG GAC ACA CAG AAA GCA CAT 202 Ile Leu Asn Asn Leu Asp Asn Phe Lys Gln Phe Asp Lys Val Phe
3258 ATT CTA AAC AAT CTT GAC AAC TTC AAG CAA TTC GAC AAA GTC TTT
```

FIG. 2A

```
          10         20         30         40         50
 1234567890 1234567890 1234567890 1234567890 1234567890
GAGCTCTACC CTTGCCTCTGC TATTGTACTT TTTAATACAC AGTTCAATCA     50
AATGTGCCAC CAGAATATGC ATGCTAACAG CTGTAGTGGT TGATTTTTCT    100
TTCTACTCTT CTGTGTGTAA GACCCCATGT TTTATCAATT ATTTTTTAAT    150
GATTTCTTTC TTCATGCATA TGTGTGGTTG TCAGTGTGAG TCTGTGTGTA    200
CAGCCAGGTGC ACAGGTATCC ACAGAGGCCA GAGGTTCCCT GTAACTAGAA   250
TTACAGGCAC TTGTGAACTT TCCTGTATGG GTGCTGGGAA GCAATCTGAG    300
GTCTTCTGCA AGGGATCTTA ACCACTGACT TTCTAGCCTG CTTTGCCCAT    350
TTCTATTTAT GATGACTGGA AACTGGGCTT AGGCCTTATA TTCTCTGAGG    400
CCAAAATCAA GTTCTTCCAA ACTGCAGGAT TTATGGTCTT CTATAGTATC    450
CCACAGAAAT GGAAAAGAAA GTGACCCATT AGAGCAGTAT TAGAGTCGAA    500
ATAAACTCAA CTTGGTATGC CAGGACTTTG GACAATAATA ACCCTGTCTT    550
TTCAGGGCAT CTATCTGTAC TGCTGCAATA GAAACTCCAC AGGTCAGGGT    600
CACAGCTGTT GTGTTTTACA CAGTGTCCCC AGGATTAGTT CAGTGCCCAC    650
CATGCAATAG GTGTCATGGT GTGTGTGTGT GTGTGTGTGC GTGTGTCGTG    700
CTTGTGTGCA TGTGTGTGAG ACACACACAC AGAGAGATAC AAAGACAGAA    750
ACAGAAAATT AATAAAATTT TACCAACTAA AATAGGGAAT TAAAGAAAAG    800
```

FIG. 2B

```
GAGGAGAAAA AGTTGGGCAT TCAACACCAT AAAGTCCCAG TACTATGCTA   850
AGAACACCCA GCTGTCCTCA CACCCGGGCA TGAAACTTCA TGCACTGTTC   900
ATCAGAAAAT CGTTTACACA CATCCCCTTG CAGTCTACTT GTAGTTTTAA   950
CAACTTCAGA GAGCACTAGC ATTTCCAGCC CCAGGTTAGA AGCTTTGGTA  1000
GATGCTGTTT GCGAGCACAG GATAGCAGCA AGAAGTGGAC TTGTTAGAAG  1050
GAAAGCCAAT GCCTATGTAA CAACGAAAAC TAAGTATGAA TCTCGAATCT  1100
CCACTCTCGT GTGTCTGTGT CTCCATATAC GTGCTTGGGT GCCTGACATG  1150
GCAAGGTGTT ACAAGTAAGG GAGGAACAAG AAAAGGACAG GGTAGTGGAC  1200
ATCAGGATGA ATGCCAGCCA GGGCGACTGG AGAGAGTCTA CGCTGCTCTG  1250
AAGGTGGGTG AAGAAGACCT CAGGAAGCTT TCTGAGGCTC CGAGAGTGCT  1300
TTTCCCTTCC CATGTTGAAA CATCCTTATT TGCAGAGAAT TCCAGGTTCA  1350
TGGGAATTTG TAAAGAGAAT ACTAAGAGGC CACCTGTGGC TTCTCCTATT  1400
TTTGTCTGCT GTCATTTATG GGACAGGGTT AGAGACCTGG CTTGCTTGGC  1450
TATGAGGCTG TTGCTTCCTC GGTTACTCTG CTGTGGTTGG ATGCATTAGG  1500
GTTAGGCCCC TCAAGAGCCA TGTGTCATTT TATAAAAGCA ATATAAATAT  1550
ACTTAAGGTG CACAAAGCAT TAGGAGGTCT GAGATAATAG ATTCTGAGAA  1600
AATCTATCCT GCTGTGTAGC AACTGATGTT TATGATTATA GTCCCAGACC  1650
```

FIG. 2C

```
          10         20         30         40         50
 1234567890 1234567890 1234567890 1234567890 1234567890
ACACGATAAA GGATCTGTGG ACTCTGTTTA GGGAGGTCAA AAAACTATTG   1700

CAAATGGAGT CTATAGAGAA AACTAGACAG GACTCAATGC TCACCAATCG   1750

AGAATTAGTT GATGAGCTGG GGTAGTGACT TAGTGGATAA GAACACGGTC   1800

CTTTCAGAGG TCCTGAGTTA AATCCCCAGC AAACACATGG TGGCTCATAA   1850

CCATCTATAT TGTGATTTGA TGCCCTCTTC TGGCATGCAG GTGTACATGC   1900

AGACTCGTAT ACATAAAATA AATAAATCTT GAAAAAATGA ATACGTTGAA   1950

TAAGTGTCCC CTCGGATAAC TTTCTGCAGA ATTTTAAGCA CATGTCAATG   2000

GTAATAACAC ACACACACAC ACACACACAC ACACACACAC ACACACATAC   2050

ACACCACCATA CAGATATGTA TCTAGAGACA TACACATGTA CATTTTATCT   2100

CTTTTATTT CTTCTCCCCT CTTTGACATC AAGGAATAGA ATGCACTCAC   2150

TGTGGCCTAG TGCCACACTC TACCTATTTC TTTGGCTTTA CTTTGTGCTA   2200

GGTGACCCGA AAGGTTTAAA TATCAAAAAT GCTAATGGCT CGACATTTAC   2250

ATCCCCAATT TCTCCTTTCT CCTTACCTCA GACTCTTACA TTCAGTTGAC   2300

AATTTGACAT CGTCTCCTGG ATTTTCAAAT GTTCAGCACA CTGTACTGAT   2350

GTACTGCCTT CCAAGGCAAC CGGCACGATC CTCTCCCCAC TCCCAAGCAT   2400

CCCTCCATGA GCCAGTGTTT GCTTATCTTC TTGACTCTTG TTTTAACCCA   2450
```

FIG. 2D

```
ACTCCCTCCCC TATTCACTCT GCTCTAATTC ATTCATTCTA TATTTTCGCA    2500
CATCAGGCTC ATCCTTTGCT CAGGAACTTC ACTTTTGCTT TCCGGTCTCC     2550
TGGAAATGTG TTTTCTTGGC TATTCCATCT CAAGACCATC TTTTCAGAAA     2600
AGCTTTTCCT ATCAACATAT TTAAAGCCCT CTTCATCCCC CAGTAGCTCT     2650
GGACACCTCA TTTTATGGAT ACACAACACA TATTTGCCAC CTGTCTCCCC     2700
ATTAAAATAT AATCTTCAGT AGAGAAACTC CATATCTTGT TAATACCTGA     2750
AACAAGAATA TCTTCAAAGA GTTCCTGGGA CATAAAAACG CTCAATTAAT     2800
ATTTATGTTA AACAGGGATC TGGGGTATAT CACAGAGGTA GAGGGCTTAC     2850
CTAGGAGGAG TTGGGCCATG GGTTCAACTT CCAGCACAGA ATGAAAGATT     2900
ATGTTAAATA AAGTTGGGAA GGATGTATGC CAGTCTATGA GTAGTATAGG     2950
AGGTAAATTA TGAATTCATA TTTACTTTTC GGACAAGAAG TGTTGTAGTC     3000
TTTATTTGAA ATAAAATACA TCTTAATTAC CAATAACAAT TGGTAAGGAG     3050
TGAATTCTCA AGCTGTGGCT TCCTGGTAGA TGAGTCCTGG GAGGTTTTCT     3100
ATTTCGATGA TGGTAGATAG GTAACCTGTC ATATACCACA TGAAATACCT     3150
GTGGCTTTGT AAACACACCG AGCAGTCAAG CAGGAGAATA GTTCCATACA     3200
GTTCGCGTCC CTTAGGATTG GTTTCGGGAT ACTTCTGGAG GTTCATTTAA     3250
ATAATTTTCC CCGAAGTACA TTATGGGCAG CCAGTGTTGT GATGGGAAGC     3300
```

FIG. 2E

```
          10         20         30         40         50
1234567890 1234567890 1234567890 1234567890 1234567890
TTCTGCCTGT TTTGCTTTGC GTCGTGCTCC ACACCTTTGA CAGATGTGCT   3350
CTCATCTGTT TACTTCTTTT TCTACACACA GAGCACAGCA TTAGCTGCTG   3400
TCCCGGCTTT GGATGTTATG TCAGCACATG AGGGACAGAC CTTCAGCTTA   3450
TCGAGTATTG CAGCTCTCTG TTTGTTCTGG AGCCTCTTCT GAGACTATGG   3500
ACTTAGTTCA AGGCCGGGTA ATGCTATTTT TTTCTTCTTT TTTCTAGTAG   3550
GAGGACAAAT AGTGTTTGCT TTGGTCACTC AAGTTCAAGT TATTGGATCA   3600
TGGTCCTGTG CACATATAAA GTCTAGTCAG ACCCACTGTT TCGGGACAGC   3650
CTTGCTTTGC TAGGCAAAGA GTCTCCCCTT TGGAAATTTT CCTGCTTTTG   3700
CAAAATGATG ACTATTTCTT TGATTTGGGG AATTGCCGTG TTGGTGAGCT   3750
GTTGCATATG GTTTATTGTT GGAATAAGGA GAAGGTATGG AAAGATTTT    3800
AAAAATTTGT CTTTTAGCTT ATTTCTAGTA TTCATTGCCT TCACTATTAT   3850
GTAGTGCAAA AAATACTAAT GCATTAATAT TTTTAAATTT AAAATTAAA    3900
GACGTACTTC TTTGACTAAA TCTAGTAAGA TGTAGAGAGT CCCCCTTGGA   3950
ACATTCACAT ATGCCACTGG TAATGCAGAT CTTGTGAAAT ATAACTAAAG   4000
AAATCACAAG TCATCGATGT AAGTTTGTGT CTGCCATGGGC GGAACAAACC  4050
TAAGCTAAGA AGAGTAGTAT TTGGGAGGGA TCTTTCTGTG ACATGAACTG   4100
```

FIG. 2F

| | | | | |
|---|---|---|---|---|
| AATAGACGCA | CTGCCTCAGC | AAACACACAT | TCATTTGAAT | TTTCCTCAGA | 4150
| CTCAGTCTAA | GCCTGGTGAG | AGCACCAAGT | GTGAGTCTGT | CTGCCACTAA | 4200
| CGTTTCCTTC | CAGTGGTAAT | CAGCTGTGTG | GCTGTGAAAC | CTTGGCGCCT | 4250
| GCACATGACA | GCCATTTGAA | TAGTTCAAAG | AACATTTAGG | GACAGGATAT | 4300
| TAAGATATTT | TCTGTGATGT | CAACATCAAA | ATAGGAGAAT | GCCCCTGGCA | 4350
| TTATCTTCAG | AGAGGTAGAC | TACTGTGCGT | TGTCTTACTT | TAAAGAAATT | 4400
| TCTTTGCCCC | TTTGGCTATT | TTAATTCAAA | CCTGAAAGTT | TTCAGTTTTA | 4450
| ATTAAACTGT | TGATTTTCAT | GCTAGGAAAG | GAAATATCAA | TTATACTTAA | 4500
| TTGTTCTTAC | AAGAAATAAA | ATCATTTATG | TCGGGAGATA | AATAAGCTCA | 4550
| TAATTTTAAT | AAAACATTTA | AGAGAGAGAA | AAAGAGTAGT | GGATTATAGT | 4600
| TCATTGTCTG | TCAATGTTTA | CCTGACCCAG | TTTCATTTTA | TAATTATCTA | 4650
| ATTTTTCAAA | TGAGATTCCT | GTTCTTTCCA | AATATCATTG | CAGAATACTA | 4700
| ACATTCTTTT | TTTCAGAGTT | GAGAATCAAA | TGGAGGGTTT | TTTCATCCTG | 4750
| GCACAAGCTC | CGCTCTTCAG | TAACACCTCC | AGCCCTCAGA | ATGCCAATAT | 4800
| TTTAAATTAT | GTAGGTTGTT | AAAACTTTAG | TGCTGGGGCT | GGGGATTTAG | 4850
| CTCAGTGGTA | GAGCACTTGC | CTAGCAAGCG | CAAGGCCCTG | GGTTCGGTCC | 4900
| CCAGCTCTGA | AAAAAAGAAA | AAGAAAAAAA | AAGAAACTTTAG | TGCTGTAGCC | 4950

FIG. 2G

```
              10         20         30         40         50
     1234567890 1234567890 1234567890 1234567890 1234567890
     CTTTCTGTTA TTTGATGTTT CACATCTGTT AAAAAACAAA ACAAAACAAA    5000
     AAAAACAAGC AAATGGAACA TTTTAGGCAT TCTTTGGGGG AAATGATTCT    5050
     TAGAGCAAGT CTAATCATTA GGTGATAGTT TCATTTTTAC ACCAAGAACA    5100
     AGAATCTTGT TGGCTGTGTT AACACTTTAA GCCCTGTTGT AGGGAAAAAG    5150
     CAATCAGACA CAGGCACAGA AAAGAATTTG GATGAGTACT TGATGATGTA    5200
     TGTATATATG GTGAATAGAC TGATGGGTGG GCTGCTGGCT GGGTTGGTAA    5250
     GTGGGTAGAT TTTTTTTTAA AGATTTATTC ATTTATTATA TATCAGTACA    5300
     CTGTAGCTAT CTTCAGATAC ACCAGAAGGG CATCGGATCT CTTTACAGAT    5350
     GGTTGTGAGC CACCATGTTT TCCTAACCTC TCAAGTCTCT GTCTTCCAGG    5400
     AAAGCTGGTG AACCTCCTTT GGAGAACGGG TTGATTCCGT ACCTGGGCTG    5450
     TGCTCTGAAA TTTGGATCTA ATCCCTCTTGA GTTCCTAAGA GCTAATCAAA   5500
     GGAAGCATGG TCACGTTTTT ACCTGCAAAC TGATGGGGAA ATATGTCCAT    5550
     TTCATCACAA ACTCCCTGTC ATACCACAAA GTCTTATGTC ATGGAAAATA    5600
     TTTTGACTGG AAAAAATTTC ATTACACTAC TTCTGCGAAG GTAATTAATT    5650
     CGTTATACAG ATTCTGTTTG TTTCCTGGTC TGTTGATGTA TTAGTGTATT    5700
     TAGTTGTTCC AATTTGTTA GGTTGCAGAA TAGAGGTAAC ATAAAATCAG     5750
```

FIG. 2H

| | | | | |
|---|---|---|---|---|
| GGCGTTTCTT | AGTAATAAGC | ATTAGACATT | TAAGGCAGAT | GTAAACCTGT | 5800
| CATTGATGAT | TCCGGAGACA | GAGGACACTG | CAGGAATCAG | GAAGGTACAG | 5850
| ATTCATAGCA | CCACTCGTCC | CTTAACAACA | CCCTGAGCAG | GGTGTTGGCA | 5900
| CTCTTAGCCT | TCAGTCCTTG | TACACACGTT | TCATTCCTAA | GATATAGGCT | 5950
| GTATATTTAA | ACACGATTTG | GAAGCCATCA | AGAATCTGTT | CTAGAGAAAA | 6000
| CAGCATTTAA | TGATCTTTTG | CAAGAAAATA | TCAGTTATAG | TCTCTGTCAT | 6050
| TAAGTACATT | GTAATCTGGT | TAAAGAGTAT | CTACTAAGAA | AGTAAAGGCA | 6100
| GATTAGAACA | ATACCAATGG | ATGATGGGCC | ATCCAGAGAA | ATCCTACTGT | 6150
| AAATGCTGGG | ATTTAAACTT | GACCCCAAGG | AAGAGTATGA | CTTGATTCTA | 6200
| CCTTTGGAAT | GTGCTGTAAA | ATCATATATTAG | GGAAGGTTCC | AGACAGAGAA | 6250
| GTGGGATGTA | TTTAATCTAT | CTTCCAGCCC | ACTCTCTAAC | ACTAGCTAGC | 6300
| TTTGGGCTTT | AGACCCTCCC | CATTTCATGG | ATTCTATTTT | CTACCAGGCA | 6350
| TTTGGACACA | GAAGCATTGA | CCCAAATGAT | GGAAATACCA | CGGAAAATAT | 6400
| AAACAACACT | TTTACCAAAA | CCCTCCAGGG | AGATGCTCTG | TGTTCACTTT | 6450
| CTGAAGCCAT | GATGCAAAAC | CTCCAATCTG | TCATGAGACC | TCCTGGCCTT | 6500
| CCTAAATCAA | AGAGCAATGC | CTGGGTCACG | GAAGGGATGT | ATGCCTTCTG | 6550
| TTACCGAGTG | ATGTTTGAAG | CCGGCTATCT | AACACTGTTT | GGCAGAGATA | 6600

FIG. 2I

```
          10         20         30         40         50
 1234567890 1234567890 1234567890 1234567890 1234567890
TTTCAAAGAC AGACACACAA AAAGCACTTA TTCTAAACAA CCTTGACAAC    6650
TTCAAACAAT TTGACCAAGT CTTTCCGGCA CTGGTGGCAG GCCTTCCTAT    6700
TCACTTGTTC AAGACCGCAC ATAAAGCTCG GGAAAAGCTG GCTGAGGGAT    6750
TGAAGCACAA GAACCTGTGT GTGAGGGACC AGGTCTCTGA ACTGATCCGT    6800
CTACGTATGT TTCTCAATGA CACGCTCTCC ACCTTTGACG ACATGGAGAA    6850
GGCCAAGACG CACCTCGCTA TCCTCTGGGC ATCTCAAGCA AACACCATTC    6900
CTGCAACCTT TTGGGAGCTTA TTTCAAATGA TCAGGTAACT TTCCAGTGAC    6950
AGAAATTGCA TTTTAAACTC AAAACCCAAA AAGACTTATA GAGCTTTCTG    7000
TGCTATCAAC AAAGAAAGTA ATACTCAATG TCCGTGTTTA GCATGTGCGT    7050
AACAGAAGCA GCAATTTTTA GGTGCACAGT CCCATCGAAA GGGATGTCCC    7100
AGAAGCCACA GAACTCAGAC AGGTTGGTGC TCCATTAGTA CAGGTTCCCT    7150
GGCCTAGTCT TGCTCCTCAC CCGATATGTT CCTCTTAATA TCAAATTAAA    7200
TCCCCGAGTG CAGTCGTCAC CACCATATAA ACATTTGAAA TGATGACTGA    7250
CTTGCAGGTG TGATAAGAGC AGTGACCATA CCTTACTAAT TCACTGGAAT    7300
```

FIG. 2J

| | | | | |
|---|---|---|---|---|
| TCATAGGCAA | AGTAACACCA | TCGATTTGT | ATTCATATAG | GAGCTGCAGC | 7350
| CATATTTTAA | ATAGCACAAC | TACTTGTTAG | TCAAGCATTC | TGAGGCTCAC | 7400
| TGTAATCAGG | TAAAGTAGGT | TTAACTCAGC | GTCCTACCAG | TTCCAGGCAT | 7450
| TGAAATGGAA | TATCCTTTAT | CCCACCCATT | CAAAACGTAA | TATATAAATG | 7500
| GAAGGCACAG | TTTTGAAGGC | CATGGTATGA | TTTAGGGAAT | TTACTCTCAT | 7550
| GGTCCAATCC | CTTGTAATTG | TATGCTAGGT | GACATATCCT | TCTGACTTAC | 7600
| TATGTTCATC | GTATATTCAA | TCCTTAGTTT | ATAGAGACTG | ACCAAAGCTC | 7650
| TGCTTTTGCA | TAGCAAAGCT | CCTTTTAATG | CCCATTCCTA | AACTCAAGGA | 7700
| CACGAATCCA | GTTCAGTGCC | CTCCCTCGCT | CTCCCTGGCA | GACTCCCGTT | 7750
| GCCATACATC | CTCCCTCGCT | CGATTCCCAT | GACCTCGCCC | TTGCACACCC | 7800
| TGGTACTAGG | ACCTCTCCTG | GCGATACTTC | CTACTACCTA | TGCCACCTCA | 7850
| TTAAAAGGAA | GGGATAATTG | CTATTTACTT | GCAGTTCTCT | GAATGAGGAC | 7900
| ATTTTCCCCA | TACGGCTCTT | TCCACAGGAG | TCCTGAAGCA | ATGAAAGCAG | 7950
| CCTCTGAAGA | AGTGAGTGGA | GCTTTACAGA | GTGCTGGCCA | AGAGCTC | 7997

ASSAY FOR AGENTS THAT AFFECT CHOLESTEROL 7ALPHA-HYDROXYLASE EXPRESSION AND A CHARACTERIZATION OF ITS REGULATORY ELEMENTS

Work related to subject matter described in this application was provided by research supported in part by NIH Grants GM 31584 and DK 44442.

CROSS REFERENCE TO RELATED APPLICATIONS

The present application is related to the subject matter of U.S. patent application Ser. No. 08/187,453 "CHOLESTEROL 7α-HYDROXYLASE GENE REGULATORY ELEMENTS AND TRANSCRIPTION FACTORS," filed Jan. 28, 1994; U.S. Ser. No. 08/135,511, "CHOLESTEROL 7α-HYDROXYLASE GENE REGULATING ELEMENTS AND METHODS FOR USING THEM," Chiang, J., filed Oct. 13, 1993, U.S. Pat. No. 5,558,999; and U.S. Ser. No. 08/361,458, GENOMIC DNA OF CHOLESTEROL 7α-HYDROXYLASE AND METHODS OF USING IT, filed Oct. 13, 1993, U.S. Pat. No. 5,663,483. The disclosures of each of these applications are expressly incorporated herein by reference in their entirety.

BACKGROUND OF THE INVENTION

High serum cholesterol is commonly associated with an increased risk of heart attack, atherosclerosis and circulatory disorders. In addition, a variety of diseases are caused by disorder of cholesterol catabolism, such as gallstone disease, atherosclerosis, hyperlipidemia and some lipid storage diseases.

The major pathway for disposal of cholesterol in the body is by secretion of cholesterol and bile acids into the gut. Bile contains free cholesterol and bile acids. The enzyme, cholesterol 7α-hydroxylase (CYP7) commits cholesterol to bile acid synthesis and catalyzes the first and rate-limiting step of bile acid synthesis in the liver. Thus, by increasing synthesis of bile acids, this enzyme plays a key role in the liver by depleting hepatic cholesterol pools, resulting in increased LDL uptake and a lowering of serum cholesterol levels.

Bile acids are physiological agents which are important in the solubilization of lipid-soluble vitamin, sterol and xenobiotics. Bile acids are synthesized exclusively in the liver and are secreted to the intestines where they are modified to secondary bile acids. Most bile acids are reabsorbed in the ileum and recirculated to the hepatocytes via the portal vein.

The feedback of bile into the liver is known to inhibit cholesterol 7α-hydroxylase and thus inhibit the overall rate of bile acid synthesis. Cholesterol 7α-hydroxylase therefore has been a subject of intense studies to elucidate the regulatory mechanisms of bile acid synthesis in the liver.

It is known that an interruption of bile acid reabsorption, such as caused by the bile sequestrant, cholestyramine, or by a bile fistula, stimulates the rate of bile acid synthesis and cholesterol 7α-hydroxylase activity in the liver. It is believed that cholesterol 7α-hydroxylase activity in the liver is regulated primarily at the gene transcriptional level by bile acids, cholesterol, hormones, diurnal rhythm and other factors.

Generally, the regulation of eukaryotic genes is thought to occur at several locations, including the promoter sequences, located upstream of the transcription start site; enhancer or repressor sequences, located upstream of the promoter; within intron sequences, non-coding sequences located between exons or coding sequence; and in 3' sequences, located downstream from the coding region. The promoter sequence is unique to each gene and is required for the accurate and efficient initiation of gene transcription. Enhancers and/or repressors regulate promoter activity and determine the level of gene transcription during development and differentiation of a particular tissue.

The promoter of most eukaryotic genes contains a canonical TATA box which binds a TFIID TATA box binding protein. TFIID complex and associated transcription activators (TAFs) interact with the basal initiation factors and RNA polymerase II to activate promoter. The transcription complex assembly and initiation are regulated by transcription factors bound to enhancer elements located in the promoter and other regions of the gene (Pugh and Tjian, J. Biol. Chem. 267, 679–682, 1992). Tissue-specific transcription factors and nuclear steroid hormone receptors are known to play an important role in the regulation of gene expression in different tissues during development and differentiation.

However, the mechanisms underlying the regulation of cholesterol 7α-hydroxylase CYP7 gene expression at the molecular level are not understood. An understanding of regulation of CYP7 gene expression would permit development of therapeutics for treating patients with defects in bile acid synthesis and cholesterol metabolism due to altered (deficient or excessive) gene expression.

In order to study the mechanism of regulation of human cholesterol 7α-hydroxylase at the molecular level, it is therefore important to determine the correct gene sequence of its coding and promoter regions. An elucidation of its gene structure and its promoter activity is sought in order to assay for an agent that modulates cholesterol 7α-hydroxylase enzyme regulation.

Beyond knowledge of the promoter sequence, a cell line is sought that is suitable for transfecting with a CYP7 regulatory element/reporter gene construct to determine the regulatory activity of a particular promoter region. Either a transiently or, more preferably, a stably transfected cell line then could be employed in a method for screening compounds for inhibiting or stimulating CYP7 expression by its direct or indirect interaction with the regulatory region, as indicated by the reporter gene's expression. In particular, a stably transfected cell line that closely mimics the physiological response of human cholesterol 7α-hydroxylase expression to bile acids would be useful and could be employed for mass screening of compounds.

A method for detecting and isolating the CYP7 transcription factors also is sought. Further, upon determining a transcription factor, an assay is desired to discover other endogenous factors or exogenous agents that interact directly or indirectly with the transcription factor. Such an assay is useful to determine factors or agents that modulate the activity of the transcription factor and thereby affect expression of cholesterol 7α-hydroxylase protein.

In addition, it would be useful to identify where important regulatory element(s) are found in the cholesterol 7α-hydroxylase gene. Such information could be used to construct a smaller version of the gene for transfecting a stable cell line. Further, such a cell line could be used in an assay to evaluate agent(s) which substantially inactivate or up-regulate CYP7 regulatory element(s). For example, an agent found to inactivate a negative regulatory element may be useful to promote increased expression of the gene and in turn, promote increased serum cholesterol degradation in a human or other mammal.

SUMMARY OF THE INVENTION

An embodiment of the invention includes a DNA sequence that comprises at least one regulatory element of cholesterol 7α-hydroxylase expression, of either human or rat origin, advantageously a fragment disclosed in Table 1.

A regulatory element according to the invention, advantageously is a bile acid responsive element. Or, advantageously, a regulatory element is a repressor or an enhancer.

Another embodiment of the invention is an abridged version of the human and rat CYP7 genes, a "regulatory minigene" as defined herein. A representative minigene, minigene-R, comprises a CYP7 fragment from −371 to a Bgl II site in intron II, measured relative to the transcription start site, +1.

Yet another embodiment of the invention is a construct having at least one regulatory element(s) described herein operatively linked to a reporter gene. An advantageous minigene/reporter construct comprises a regulatory minigene operably linked to a reporter gene. Such a construct preferably is stably transfected into a hepatic-derived cell line to provide a cell line useful for assaying numerous compounds. Additionally, other CYP7 regulatory elements can be used. A promoter/reporter construct can be transiently or stably transfected into a hepatic-derived cell line.

In an advantageous assay according to the invention, agent(s) that inhibit or stimulate CYP7 expression are detected by contacting a stable cell line transfected with a minigene construct, and culturing the cell line under conditions suitable for gene expression. Then, the activity of the regulatory minigene is monitored to provide information as to how the agent affects expression.

Another embodiment of the invention includes subfragment(s) of any regulatory element disclosed in Table 1 that can maintain regulatory activity. That is, the subfragment can function either as a bile acid responsive element or, as an enhancer or repressor when exposed to a hormone, protein kinase C activator or other compound that exerts an effect on native CYP7 gene. Regulatory activity can be detected by a HepG2 transient transfectant assay described herein. For example, a regulatory subfragment of the human fragment −79 to −34 includes a bile acid responsive element at least from about −64 to about −54.

Yet another embodiment provide methods for isolating a transcription factor of the cholesterol 7α-hydroxylase gene. Advantageously, the methods of detecting, substantially isolating and assaying for a CYP7 transcription factor, employ transient HepG2 transfectants cultured to confluency or a cell line stably transfected with a regulatory minigene.

BRIEF DESCRIPTION OF THE DRAWINGS

FIG. 1 shows the sequence of the human CYP7 gene, (SEQ ID NO:5) including Xba I and Bgl II restriction sites.

FIG. 2 shows a rat genomic sequence of the rat CYP7 gene (SEQ ID NO:7) taken from a R7αB24, deposited as clone R7αB24 on Jan. 28, 1994, at the American Type Culture Collection, (ATCC), 12301 Parklawn Drive, Rockville, Md. 20852, U.S.A., under accession number ATCC 69546.

In FIG. 2 only, the numbering system begins with the first nucleotide of the clone, not the transcription start site as conventionally depicted. In the figure, the transcription start site "G" is located at nucleotide position 3644; Exon I is 3644–3784; Exon II, 5400–5640; Exon III, 6348–6934; and Exon IV, 7928–7997.

DETAILED DESCRIPTION OF THE PREFERRED EMBODIMENTS

It was found that the promoter region located downstream of a conserved Hind III site in human and rat CYP7 genes is very important in controlling transcription of the respective species of gene. That is, a set of regulatory elements were identified in the region downstream from about −371 to about +24 of the human CYP7 gene, and downstream from about −349 to about +24 of the rat CYP7 gene.

According to the present invention, the term "regulatory" means a characteristic ability of a CYP7 DNA fragment to exert transcriptional control of a CYP7 gene in the presence of a factor known to either down-regulate CYP7 expression, e.g., bile salts or mevinolin, or up-regulate CYP7 expression, e.g., cholestyramine, bile fistula or cholesterol. According to the present invention, a "regulatory element" DNA fragment is (i) a bile acid responsive element, (ii) a repressor or (iii) an enhancer, or can function as any combination of i, ii or iii.

Advantageously, a recombinant construct is provided that includes a regulatory minigene. The key elements of a "regulatory minigene" include its having at least one or more of the bile acid responsive elements (i) from about from about −371 to about −221, (ii) from about −173 to about −129 and (iii) from about −79 to about −34, together with elements including a TATA box core region (shown in FIG. 1), intron I, and intron II, from beginning to the Bgl II splice site. It is also contemplated that a functional minigene could be made which provides the bile acid responsive elements (i) and (ii); (i) and (iii); (ii) and (iii), together with the other elements listed herebefore. However, use of all three bile acid responsive elements and all CYP7 nucleotide sequences that link the elements described is advantageous to provide optimal physiological CYP7 performance in the assay described herein. Thus, minigene-R is advantageously used.

Figure 3:
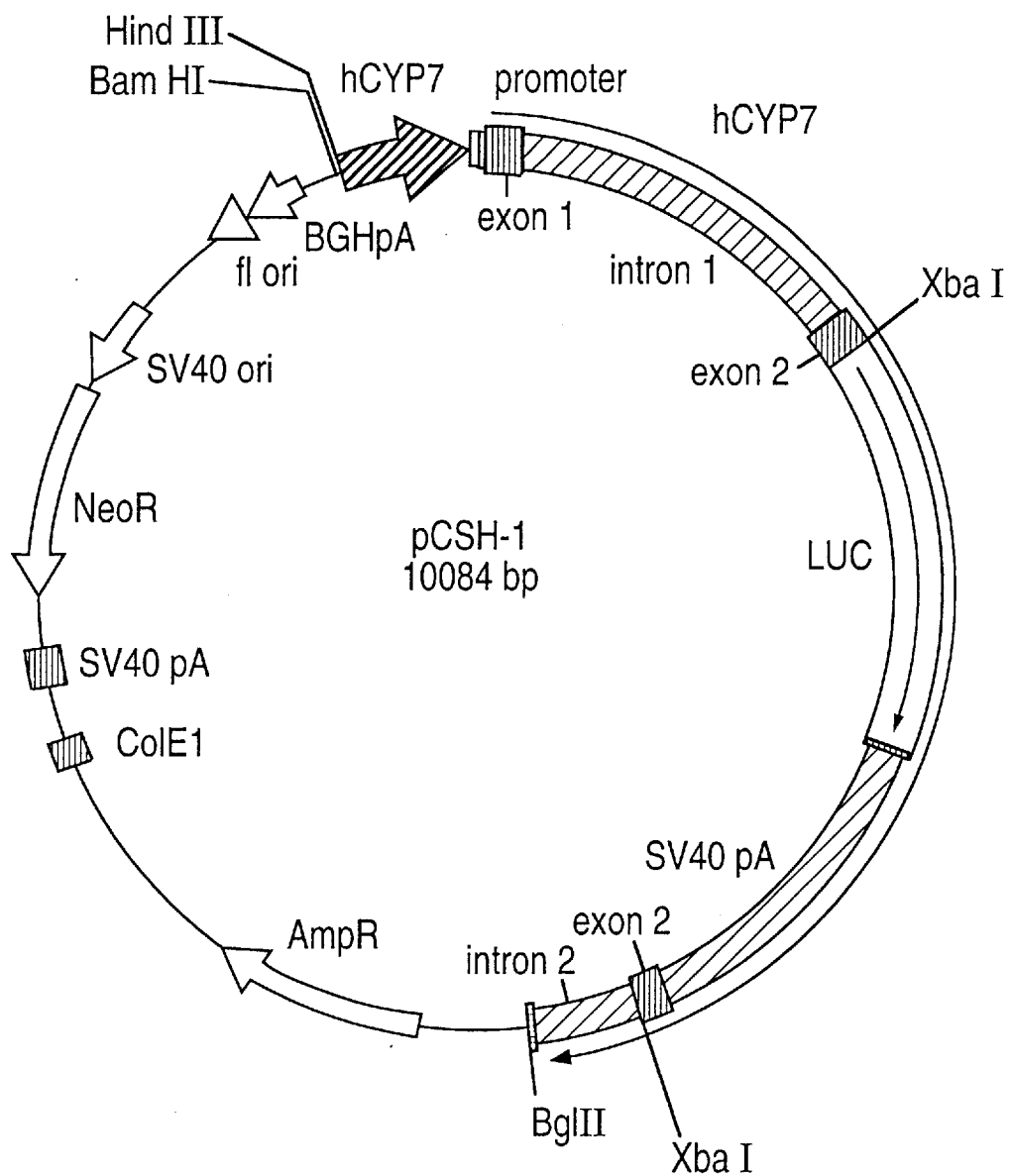
FIG. 3 shows a minigene-R construct pCSH-1 of human CYP7 regulatory element from −371 to a Bgl II cleavage site located in the middle of intron II, (including intron I), that is ligated to luciferase gene.

A representative minigene advantageously employed in a construct is "minigene-R" which in human comprises the nucleotides downstream from −371 to the single Bgl II site in intron II, and in rat from −344 to the single Bgl II site in intron II. Minigene-R, shown in FIG. 3, can be made, for example, according to Example 1. A regulatory minigene larger than minigene-R further can be made by adding consecutive nucleotides from CYP7 at either or both ends of minigene-R, or by adding exons II–VI to the Bgl II site end.

Also, a recombinant "promoter" construct is provided that includes one or more regulatory element(s) from the promoter region of CYP7 and that is suitable for transfecting a host cell. Such a construct includes a regulatory element disclosed in Table 1 (other than minigene-R) or a combination of one or more of such regulatory elements. In a recombinant construct according to the invention, a regulatory element is operably attached to a reporter gene, marker gene etc., as is conventional. Thus, "promoter/reporter" and "minigene/reporter" constructs are provided. "Operably attached" means that the regulatory element is positioned with respect to the gene such that it exerts transcriptional control over it. Another embodiment is a host cell transiently or stably transformed or transfected with a recombinant construct according to the invention. In a preferred embodiment, a hepatic-derived cell, such as a hepatoma cell, is stably transfected with a minigene/reporter construct to provide a transfected cell line (transfectant). Such a transfectant is useful for assay purposes.

In an assay according to the invention, a stable minigene transfectant is contacted with a test compound(s) and cultured under conditions suitable for gene expression to determine the regulatory effect of the compound(s). A test compound can comprise, for example, a physiological agent derived from compounds that are endogenous or exogenous to humans. The CYP7 regulatory minigene controls expression of a reporter gene. The affect of the compound thus is exhibited by inhibition or stimulation of reporter gene expression, as detected by conventional methodologies, e.g. measuring luciferase activity.

The development of stable minigene transfectants permits large scale testing of compounds. Advantageously, compounds can be administered robotically to individual cell lines provided in a grid format. Compounds can be assayed one at a time, or as a combination of two or more different compounds. A preferred stable cell line for use in such an assay is transfected with minigene-R, "HepG2/2.2.1", deposited as ATCC #CRL 11997, on Nov. 21, 1995, described in Example 2.

In another embodiment, hepatic-derived cell lines, advantageously HepG2 cells, are transiently transfected with a promoter/reporter construct according to the invention. By observing expression in HepG2 cultures transiently transfected with CYP7 promoter/reporter gene constructs, the activity of a particular regulatory element region can be ascertained. Further, an agent can be added to the transfectant, and its effect on transcription can be ascertained readily.

Transient promoter/reporter transfectants to be used in an assay should be cultured to a "confluent" state. Confluent cells are defined as cells that are cultured to at least about 4 days old, preferably 5 days old, relative to the initiation of transfection. Confluent cells alternatively can be recognized by their uniform growth pattern, where cells tend to "adhere" to one another. In transient promoter/reporter transfectants, the age of HepG2 transfectant cultures had a significant effect on the cells' response to steroid/thyroid hormones or bile acid conjugates. Younger cells were found to be less responsive to hormones and bile acids, possibly due to an underdeveloped or undeveloped bile acid transport system and/or an immature steroid hormone receptor system.

Figure 5:
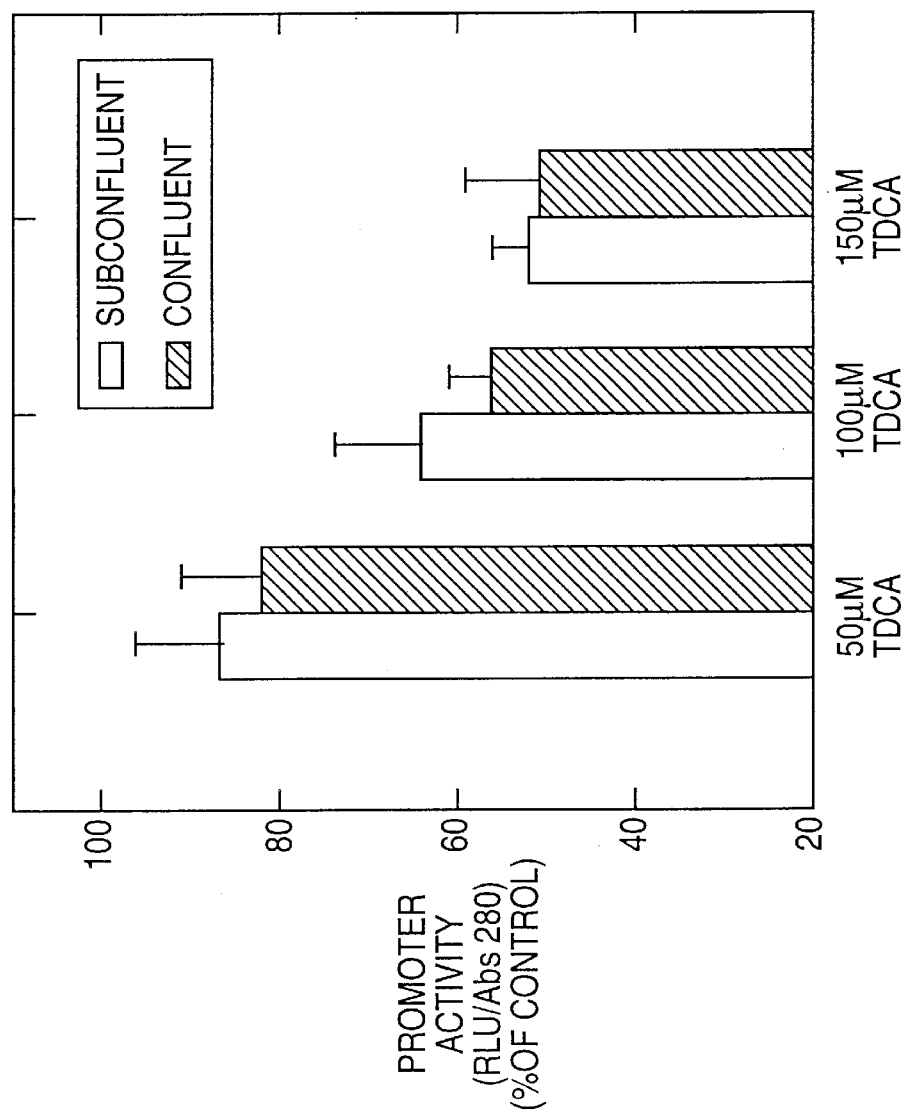
FIG. 5 demonstrates the difference between a confluent and subconfluent cultures of HepG2 cell lines stably transfected with the minigene-R, in the presence of the bile acid TDCA.

In contrast, the confluency of stable minigene/reporter transfectants was less important than for transient transfectants of promoter/reporter constructs. As shown in FIG. 5, non-confluent cells performed similarly as did confluent cells. The difference, in part, may be due to the presence the minigene's intron(s), or to the stable nature of the cell lines. In any event, it is not required to culture these transfectants to confluency. Therefore, costs and labor savings can be achieved through use of non-confluent cultures of minigene transfectants.

Regulatory elements were located in the human and rat sequences using the transient and stable transfectants described above containing deletion mutants of human or rat CYP7. The sequence of the human and rat CYP7 genes are known. The human sequence, shown in FIG. 1 (SEQ ID NO:5), was disclosed by Wang et al, *Genomics* 20: 320–323 (1994), and deposited as Genbank Accession Numbers L20569 and L20570. The rat sequence, shown in FIG. 2, was disclosed by Chiang et al. *Journal of Biochemistry* 269: 17502–17507 (1994) and deposited as Genbank Accession Numbers U01962. These publications and Genebank accessions are expressly incorporated by reference herein in their entirety.

Advantageously, three bile acid responsive elements ("BAREs") were identified in the human and rat genes. Human BARE fragments were found from about −371 to about −221, from about −173 to about −129, and from about −79 to about −34. Correspondingly, in the rat gene, bile acid responsive elements were found from about −344 to about −222, from about −174 to about −129, and from about −72 to −32.

Further, repressor and enhancer fragments were identified in human and rat genes, and their regulatory activity is demonstrated in FIGS. 8–11. In the human gene, one repressor sequence was found at about −371 to about −298, and another repressor at about −150 to about +24. An enhancer was found at about −298 to about −150.

Figure 12:
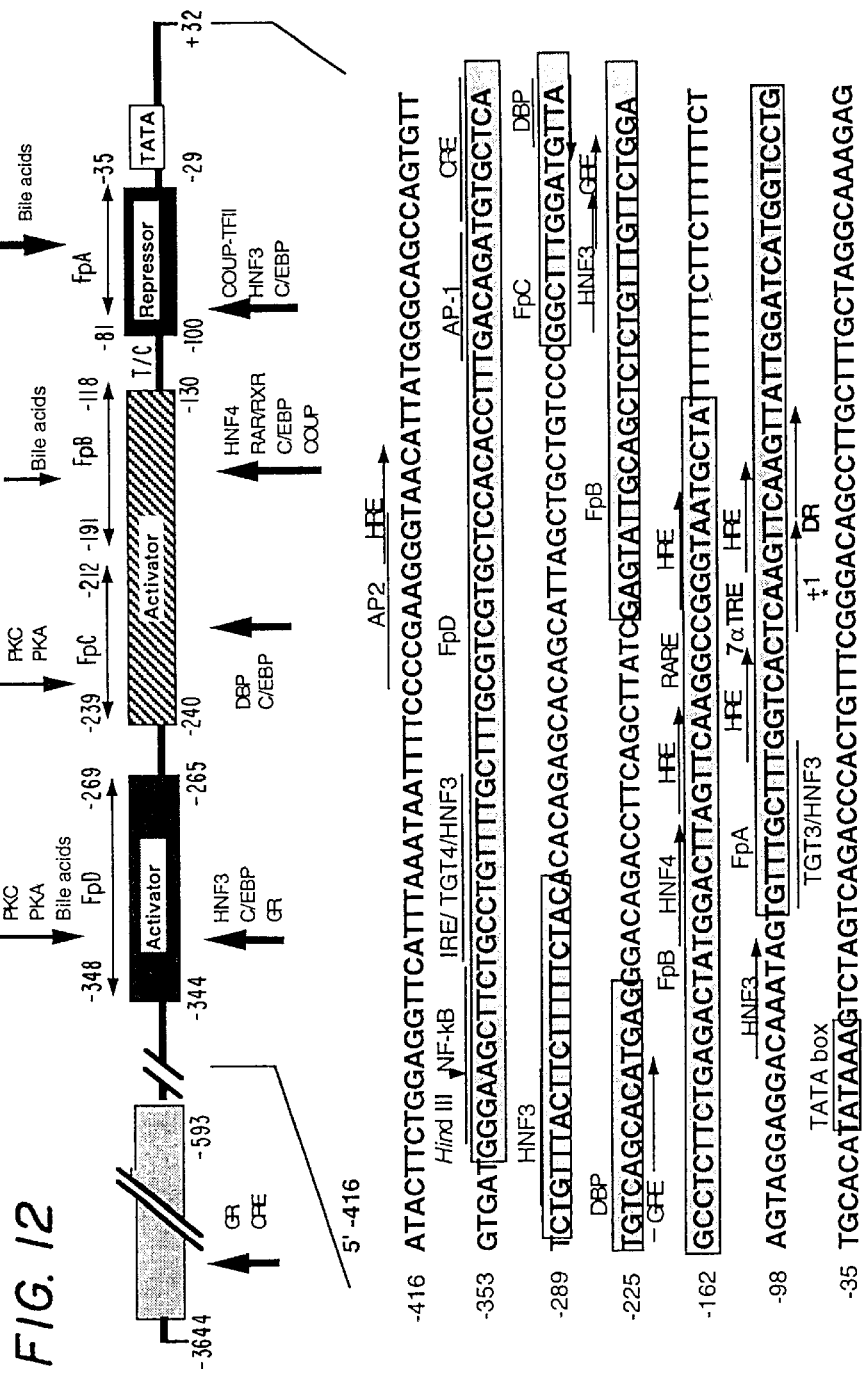
FIG. 12 shows a diagrammatic representation of regulatory elements of the rat CYP7 gene. (SEQ ID NO:8)

In the rat gene (SEQ ID NO:7), a first enhancer fragment was found at about −344 to about −265. A longer version of that fragment, from about −344 to about −222, also exhibited enhancer activity. Another enhancer was found at about −240 to −129, and a repressor from about −81 to about −35, as shown in FIG. 12.

The bile acid responsive elements from about −72 to about −32 of the rat, and from about −79 to about −34 of the human gene correspondingly, were characterized further. Both fragments were shown to bind to a bile acid responsive protein (BARP) and also contain COUPTF-II binding sites, further confirming the regulatory nature of the fragments. An essential subfragment of this bile acid responsive element bound to BARP and was identified as the direct nucleotide repeat "$DR_0$."

In the human gene (SEQ ID NO:5), $DR_0$ is nucleotides −65 to −54, CCAAGCTCAAGT, and in the rat (SEQ ID NO:7) nucleotides −64 to −53, TCAAGTTCAAGT. A consensus "core" nucleotide sequence that emerges from the two species of the molecule is (T or C)CAAG(T or C).

A COUP-TFII binding site was identified within the region spanned by bile acid responsive element from about −72 to about −32 of the rat, and from about −79 to about −34 of the human gene correspondingly. The presence of a COUP-TFII site further indicates this region's regulatory nature. COUP-TFII is a member of a nuclear receptor supergene family, and binds to CYP7 in particular between about −74 to about −53 in the human and from about −72 and about −52 in the rat. COUP-TFII may function in determining the level of CYP7 transcription in various species of mammals.

Another advantageous regulatory element of the rat CYP7 gene is any DNA fragment selected from the group of fragments having regulatory activity and consisting of the fragments listed in Table 1, or regulatory subfragments thereof. It is noted that the regulatory elements as identified in Table 1 do not necessarily end or begin at the precise endpoints listed in the Table. That is, larger fragments on the order of at least 5–10, perhaps even 10–20 nucleotides longer, can be made that encompass the listed fragments without negating the fragment's activity. Hence, the endpoints of the fragments are referred to as existing from "about" a certain nucleotide numerical position to "about" another nucleotide position. The minigene, however, can be made substantially longer as discussed below.

TABLE 1

RAT & HUMAN CYP7 REGULATORY ELEMENTS

| I<br>RAT<br>SEQ ID NO: 5 | II.<br>Human<br>(SEQ ID NO: 4)<br>(from transcript. start site) | |
|---|---|---|
| −344 to −222 | −371 to −221 | |
| −174 to −129 | −173 to −129 | Bile acid responsive elements |
| −72 to −52 | −79 to −34 | |
| −64 to −53 | −65 t0 −54 | |
| −344 to bgl II (mid-intron II) | −371 to Bgl II site (mid-intron II) | Minigene-R |
| −344 to −265 | −371 to −298 | |
| −344 to −222 | −298 to −150 | Repressors or enhancers |
| −240 to −129 | | |
| −72 to −32 | −150 to +24 | |

A method for detecting whether a fragment of CYP7 or subfragment thereof has regulatory activity comprises first providing a fragment for test purposes, for example, by making a deletion mutant with restriction enzymes or by using PCR. Next the test fragment is ligated to a suitable reporter gene, preferably luciferase. Next the promoter/reporter construct is transiently transfected into a hepatoma cell, preferably hepatoma HepG2 cells. Such cells then are grown to a confluent state.

Next, transient transfectants are exposed to bile acids such as taurodeoxycholate ("TDCA"), and transcriptional activity of the test fragment is monitored to detect reporter gene expression. Endogenous agents, or exogenous agents thought to effect CYP7 can be added, such as insulin or phorbol ester, etc., and the regulatory affect monitored.

Other substantially identical sequences will have CYP7 regulatory activity and can be tested as described above. Upon exhibiting regulatory activity, such sequences can be employed as are the regulatory elements identified specifically herein. Exemplary substantially identical sequences include those that share nucleotide identity with respect to the described fragments: of at least about 80%, advantageously about 90% and more advantageously about 95%.

Additionally, a comparison of rat and human sequences is found in Crestani et al. *Arch of Biochem. Biophys.*306: 451–460 (1993). This publication is incorporated by reference in order to demonstrate homologous sequences between the two species.

The following examples merely illustrate the invention and, as such, are not to be considered as limiting the invention set forth in the claims.

EXAMPLE 1

A Human Regulatory Minigene Construct

Restriction enzyme digestion of pHG7α5.0 (Wang et al, supra.) was performed with Hind III/Bgl II to yeild a human CYP7 fragment which was purified by agarose gel electrophoresis. The resultant fragment, "Minigene-R" contained sequences from nucleotide −317 (Hind III) to Bgl II site in the middle of intron 2 (FIG. 1).

The Xba I site in the pCDNA3 vector (Invitrogen, San Diego, Calif.) was removed by digestion with Xba I and then treated with Mung Bean nuclease. DNA was religated with Klenow fragment and transformed into JM101 (Stratagene, La Jolla, Calif.).

The modified vector plasmid was selected by mapping of Xba I and EcoRI sites. The CMV promotor in PCDNA3 was removed by digestion with Hind III and Bgl II. The remaining 4.7 kilobase fragment of the vector and the 2.7 kilobase Hind III to Bgl II fragment of the gene were ligated and subsequently transformed into JM101. The positive clone was selected by restriction digestion with Hind III and Bgl II to confirm the presence of insert in the construct. This construct was then digested with Xba I and dephosphorylated with calf intestinal alkaline phosphatase.

A 2.8 kilobase fragment containing the luciferase gene and SV40 polyA signal was removed from pFlash I vector (SynapSys Burlington, Mass.) by digestion with Spe I and Sma I. This luciferase gene fragment was inserted into the Xba I site in the exon 2 of the gene construct.

The resultant pCSH-1, as shown in FIG. 1, containing human minigene-R and luciferase reporter gene was transformed into JM101. Positive clone was selected and the orientation of the insert was confirmed by digestion with Bam HI. The promoter activity of pCSH-1 was confirmed by expression of luciferase in transient HepG2 transfectants.

EXAMPLE 2

HepG2/2.2.1 (Minigene-R) Stable Transfectants

The construct of Example 1, pCSH-1, was transfected into HepG2 cells. Stable cell lines carrying this contruct were selected for resistance to G418 and expression of luciferase activity according to the method described by Ausubel et al., CURRENT PROTOCOLS OF MOLECULAR BIOLOGY Wiley Intl., Chapter 9.5.1–9.5.5 (1993). Cells were plated at 4,000 cells/well in 6-well culture dishes and G418 was added to the culture at 40 mg/ml. Confluent HepG2 cells were split 1/15 into 4×10 cm dishes containing 12 ml DMEM/F12 medium supplemented with 10% fetal bovine serum and 1× Penicillin/Streptomycin 24 hours prior to transfection. Medium was changed 1 hour prior to transfection. Cells were transfected with 25 microgram DNA/well using Ca+ phosphate coprecipitation method and incubated in complete medium for 48 hours. Cells were splited 1/15 into complete medium plus 400 microgram/mil G418 and plated at $5 \times 10^5$ cells/plate. Medium was changed every 5 days to remove dead cells and stable colonies were picked after 17 days and plated in 12 well plates in 2 ml complete medium supplemented with 133 µg/ml G418. Cells were grown to confluency and splited into 12 well-plates. Cultures were maintained at 200 µg/ml G418. Luciferase activity in selected stable cells was assayed for luciferase activity. To test if the luciferase construct has properly integrated into the chromosome, the positive clones were tested by digesting the chromosomal DNA with Hind III and Southern blot hybridization was performed. The 1.7 kb EcoRI fragment of the luciferase gene was used as a probe. Positive cell lines were expanded and tested for the expression of luciferase activity. A stable cell HepG2/2.2.1 which expressed a luciferase activity of about 66% of the promoter activity of p-1.9Luc construct in HepG2 was selected for testing the effects of bile acids and hormones and deposited.

EXAMPLE 3

Physiological Response of HepG2/2.2.1 Stably Transfected Cells

A. Bile Acids

Figure 4:
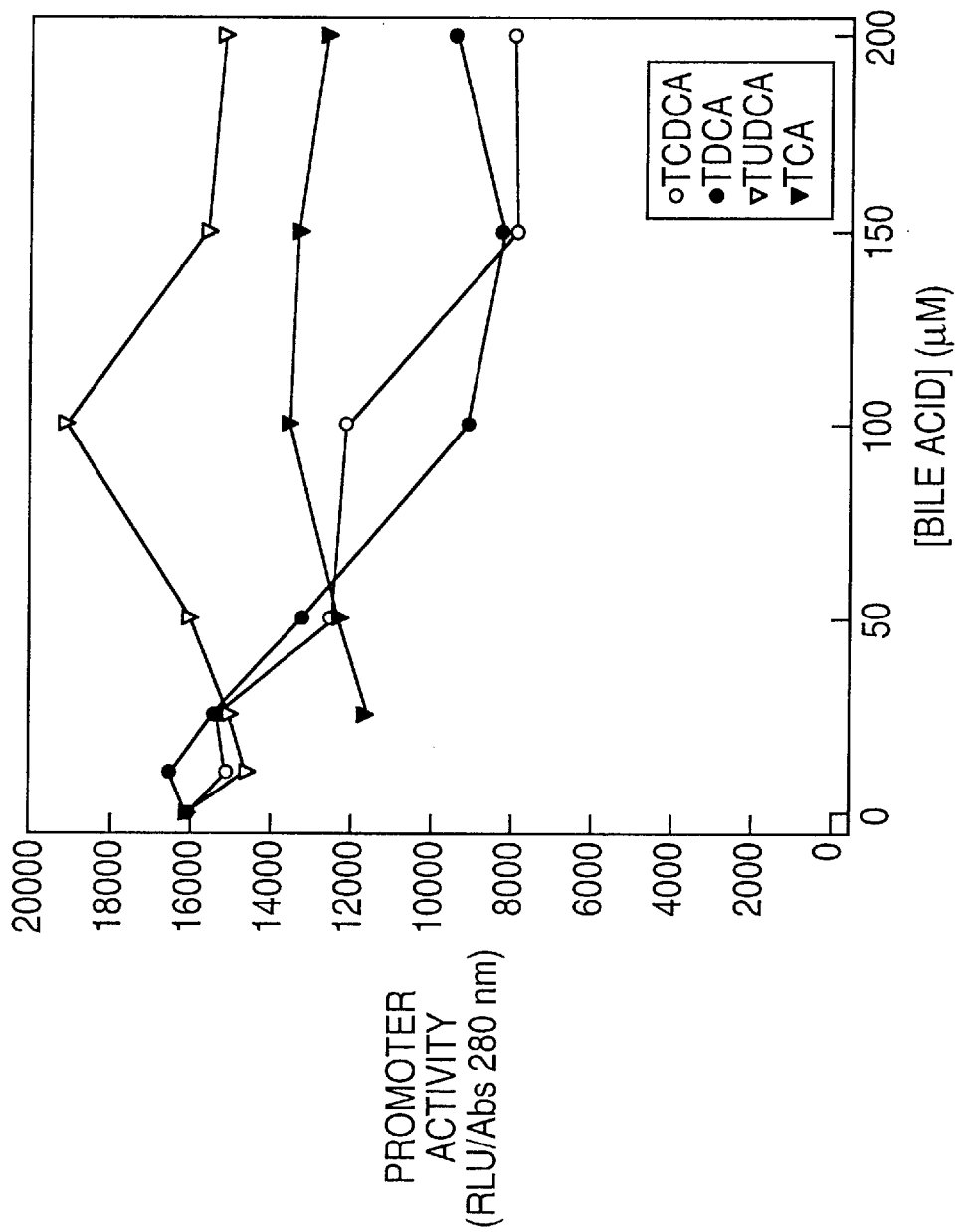
FIG. 4 shows the effect of four different bile acids on a confluent culture of HepG2 cell line stably transfected with the minigene-R. Shown are taurochenodeoxycholate (TCDCA), taurodeoxycholate (TDCA), tauroursodeoxycholate (TUDCA) and taurodeoxycholate (TDCA).

The effects of different bile acids on the human CYP7 minigene-R were tested and are shown in FIG. 4. These results closely mimick the physiological response of CYP7 as demonstrated in transient transfectants. Chiang et al., *Journal of Biochemistry* 269: 17502–17507 (1994) That is, the more hydrophobic bile acids, TCDCA and TDCA, exert a more inhibitory effect than hydrophilic bile acids, TUDCA and TCA.

The inhibitory effect of bile acids follows the hydrophobicity indexes of bile acids, TUDCA<TCA<TDCA<TCDCA, as described by Heuman et al., *Lipid Res.* 30: 1160 (1989). The results are also consistent with those observed in primary cultures of rat hepatocytes, as described by Hylemon et al., *J. Biol. Chem.* 267: 16866 (1992).

In the present experiments, the bile acids TCDCA, TDCA TUDCA and TCA were administered in 50 micromolar incremental amounts, from 0–200 micromolar. Their regulatory effects were observed as luciferase activity, measured by a luminometer.

B. Insulin

Figure 6:
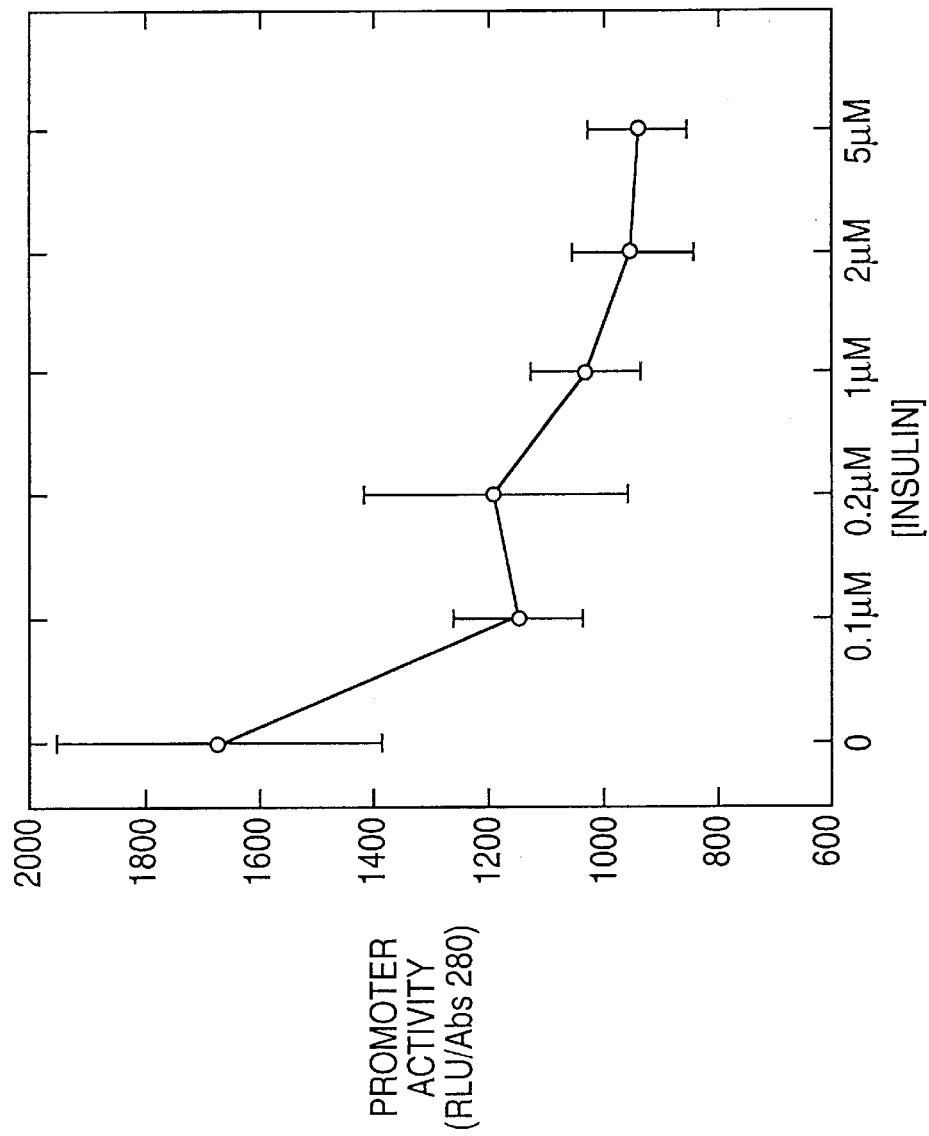
FIG. 6 shows the effect of insulin dosage on a confluent culture of HepG2 cell line stably transfected with minigene-R.

Insulin was applied in dosages of 0, 0.1, 0.2, 1, 2, and 5 micromolar to minigene-R stable transfectants (confluent culture) and repressed CYP7. Results are demonstrated in FIG. 6.

The inhibitory insulin response seen in the minigene-R transfectants corresponds with that of seen in human diabetic patients.

C. Phorbol esters

Phorbol 12-myristate 13-acetate (PMA) is a known activator of the physiological regulator, protein kinase C. Investigators have reported that CYP7 gene may be mediated by protein kinase C. Stravitz et al., *J. Lipids Research* 36: 1359–1368 (1995). Therefore, the regulatory response to PMA was investigated.

Figure 7:
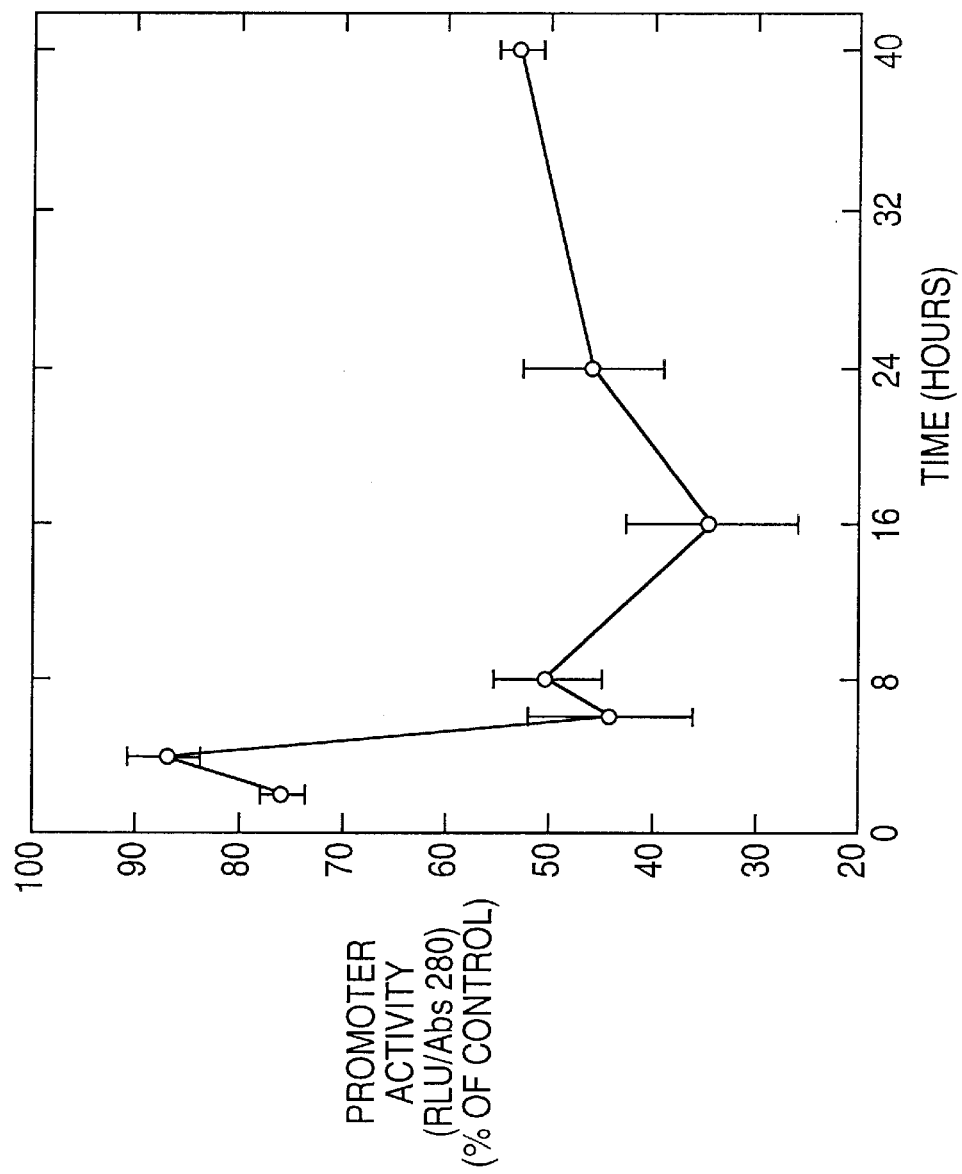
FIG. 7 shows that phorbol 12-myristate 13-acetate (PMA) represses CYP7 activity in a confluent culture of HepG2 cell line stably transfected with minigene-R.

PMA was applied to minigene-R stable transfectants (confluent culture) in dosage of 1 micromolar. Over a time course of 8 hour increments up to 40 hours, PMA showed maximal repression of CyP7 at 16 hours. Protein kinase C indeed may be involved in repression of CYP7 at bile acid responsive element, −298 to −150. Results are demonstrated in FIG. 7.

EXAMPLE 4

Characterization of Regulatory Elements by Responses of Human Deletion Constructs A. Human Chimeric Deletion Constructs First, a 1.9 Kb 5'-flanking region of human CYP7 gene was obtained by polymerase chain reaction (PCR) amplification using a human CYP7A1 clone pHG50K as a template Wang et al., supra. In the PCR reaction, the primers used were 5'-primer, 5'-CGGGGTACCTGAGATTTGGAT-GGGGACACA-3' (SEQ ID NO:1), and 3'-primer 5'-TAGGAAGGGAAAGATTAGTGAGCTCGCCAT-3' (SEQ ID NO:2).

Restriction enzyme recognition sequences for KpnI (−1877) and XhoI (+24) were introduced into 5' and 3'-primers, respectively, for generating cloning sites. The 1.9 Kb PCR product (−1877 to +24) was purified by glass bead, digested with KpnI and XhoI, and ligated to XhoI-KpnI-digested luciferase reporter gene vector pGL2-basic (Promega, Madison, Wisc.). The nucleotide sequences of this chimeric construct, pLUC-1877/+24, were confirmed by DNA sequencing.

The construct pLUC-1723 (EcoRV) was generated by restriction digestion of pLUC-1877 with EcoRV and XhoI and ligated into SmaI- and XhoI- digested pGL2-basic. Another construct, pLUC-298, was picked up randomly from this plasmid minipreparation.

The pLUC-785 (Spe I) and pLUC-371 (Hind III) were generated by restriction digestion of pLUC-1877 with Spe I and Hind III, respectively, filling-in with Klenow fragment of DNA polymerase I, and then digested with Xho I. Fragments were generated bearing a 5' blunt-end and a 3' Xho I site.

The generated fragments were cloned into pGL2-basic vector cut with Mlu I, blunt-ended by filling-in with Klenow and digested with Xho I. The construct pLUC-150 was made by PCR, using a human pHG5.0K as a template. The 5' primer was 5'-TCGGGGTACCTGTGGACTTAGTTC-AAGG-3' (SEQ ID NO:3) tagged with a KpnI restriction site (italicized). The 3' primer was 5'-TACCGCTCGAGT-GATTAGAAAGGGAAGGAT-3' (SEQ ID NO:4) tagged with a Xho I restriction site (italicized).

The PCR product was digested with KpnI and EhoI, and cloned into KpnI and XhoI sites of pGL2-basic plasmid. All the constructs were verified by restriction digestion analysis and the sequences were confirmed by sequencing. Chimeric genes were also constructed using a newly available pGL-3 basic vector (Promega) which was modified from the original pGL2-basic vector and expresses a much higher luciferase activity.

The ph-1887Luc was obtained by linking a EcoRI (−1887) to Hind III (−371) fragment to a PCR product containing Hind III/Xho I(+24), blunt-ended, and cloned into Nhe I(blunt)/Xho I cut-pGL3 basic vector. The ph-3025Luc was constructed by linking a PstI (−3025) to HindIII fragment to a Hind III/Xho I fragment. The ph-785Luc (SpeI/XhoI), ph-371(HindIII/XhoI), ph-298 (KpnI/XhoI) and ph-150(KpnI/XhoI) were also obtained by cloning the fragments into NheI (blunt)/XhoI or KpnI/XhoI cut-GL3 basic vector.

Figure 8:
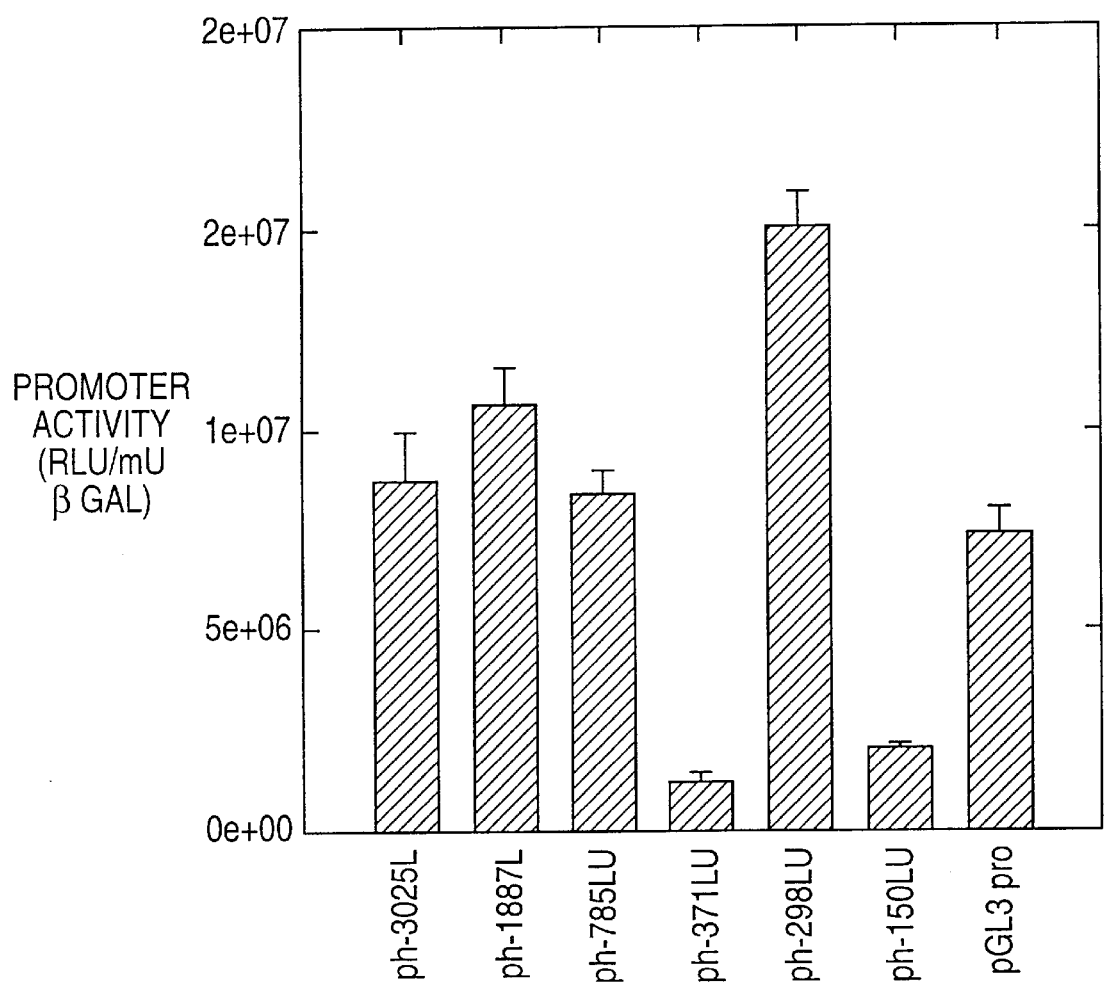
FIG. 8 shows the basal level of promoter activity of human CYP7/LUC deletion constructs in transiently transfected HepG2 cells.
Figure 9:
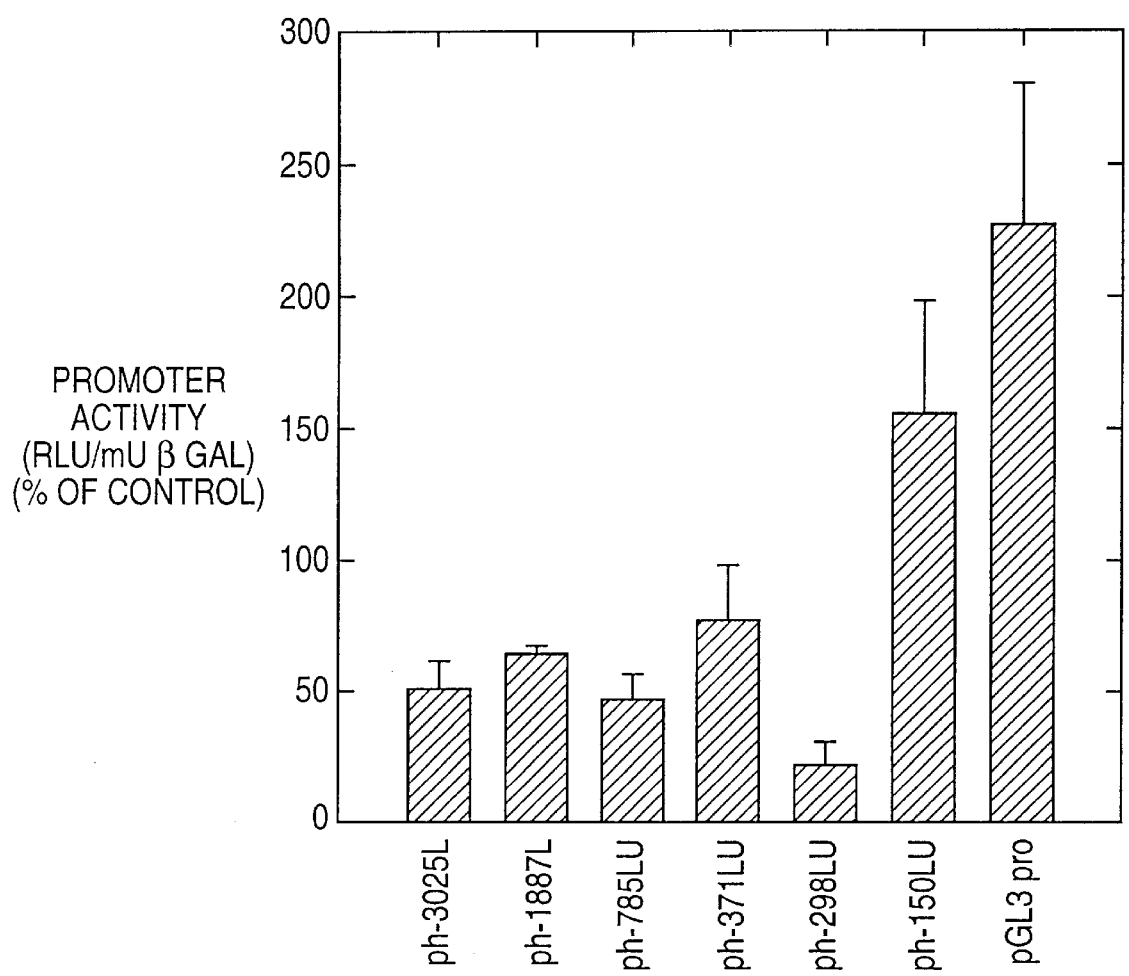
FIG. 9 shows the effects of insulin on the activity of human CYP7/LUC deletion constructs in transiently transfected HepG2 cells (expressed as of control).
Figure 10:
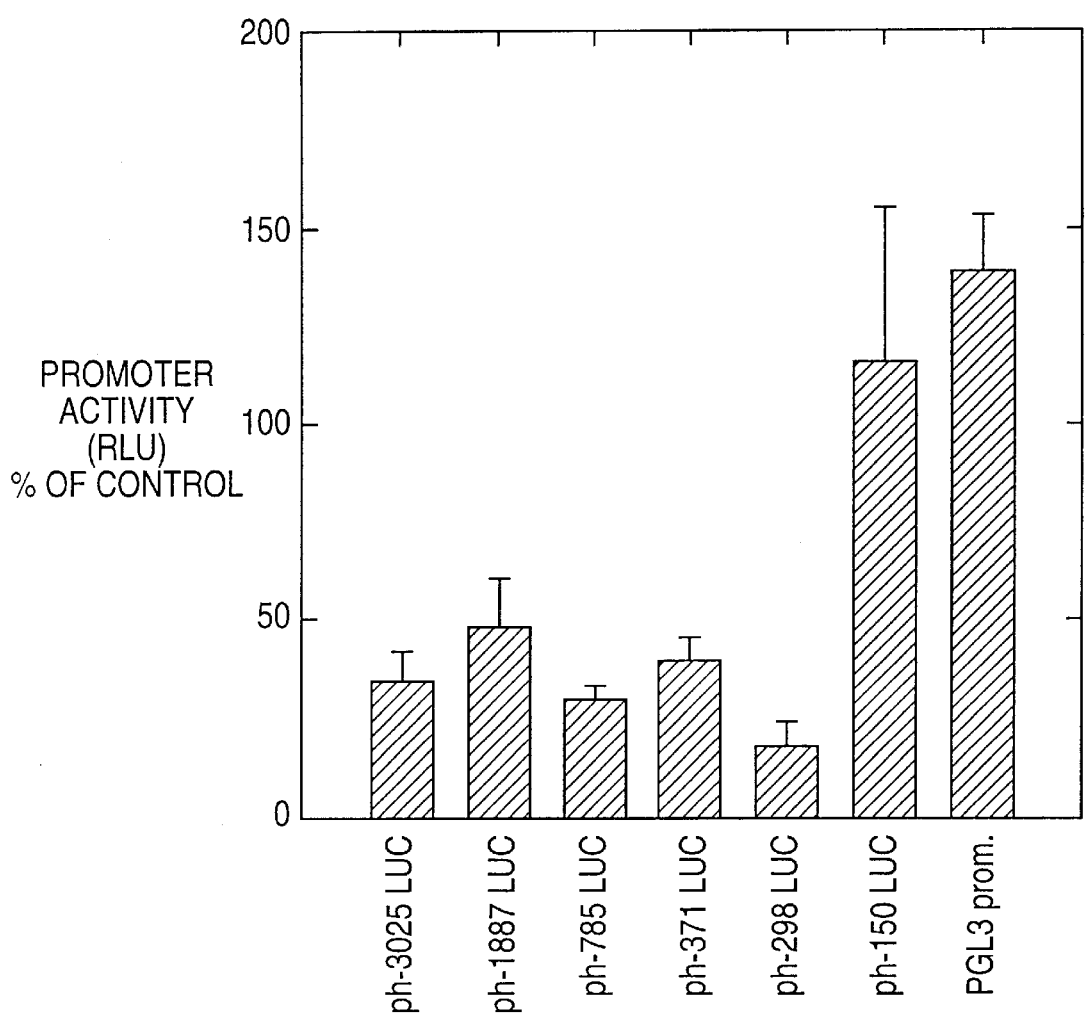
FIG. 10 shows the effect of phorbol ester PMA on human CYP7/LUC deletion constructs in transiently transfected HepG2 cells, at 16 hours post-application (expressed as of control).
Figure 11:
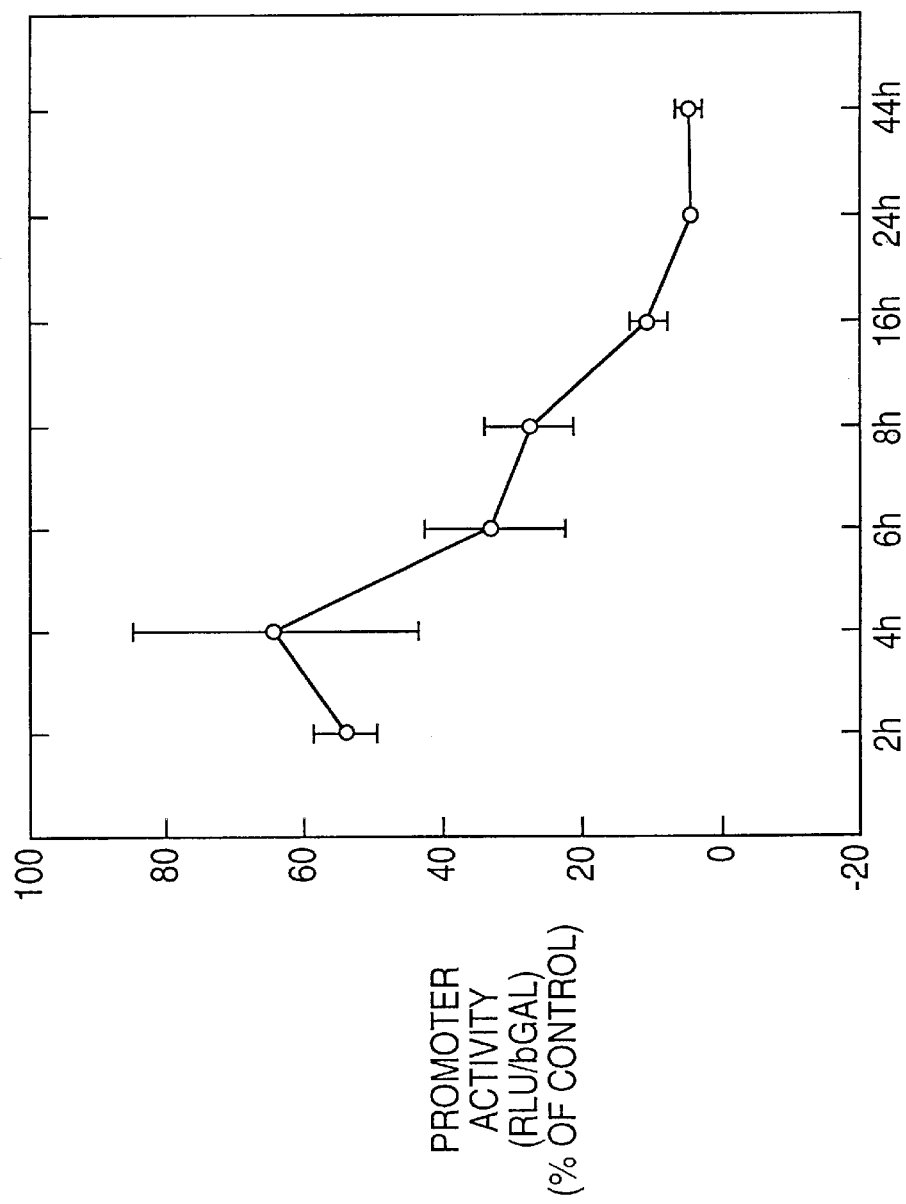
FIG. 11 shows a time course of the repressive effects of phorbol ester PMA on human construct p3025//LUC in transiently transfected HepG2 cells (expressed as of control).

An initial basal level of promoter activity of human CYP7/LUC deletion constructs in transiently transfected HepG2 cells was determined. Results are shown in FIG. 8.

EXAMPLE 5

Footprinting

DNase I footprinting technique provides further evidence of the significance of the regulatory elements described herein. Footprinting is applied to map the transcription factor binding sites in the promoter region. Heberlein et al. *Cell,* 41, 965–977, (1985). Transcription factor binding sites in the gene are protected from DNase I digestion.

Probes are made from plasmid DNA digested with a restriction enzyme to generate a 5'-overhang, filled in with the Klenow fragment of DNA polymerase I and $^{32}$P-labeled dCTP, and then digested with a second restriction enzyme.

Probes are purified from a native 5% polyacrylamide gel. Footprinting reactions included 2 μg of poly(dI-dC), 10% polyvinyl alcohol, 50 mM KCl and 20 fmol of probe in a volume of 50 μl. Reactions are stopped with EDTA and SDS, then phenol extracted, ethanol precipitated and run on polyacrylamide sequencing gels.

The footprinted areas that were detected in rat CYP7 are summarized in FIG. 12 (SEQ ID NO:8), as follows:

Footprint A (FpA), nucleotides −81 to −35, namely, 5'-TGTTTGCTTTGGTCACTCAAGTTCAAGTTAT-TGGATCATGGTCCTG-3'.

Footprint B (FpB), nucleotides −191 to −118.

Footprint C (FpC), nucleotides −239 to −212.

Footprint D (FpD), nucleotides −348 to −259.

The footprints A and B identified above confirm certain of the results disclosed in U.S. Ser. No. 08/187,453. Only footprints identified therein as "I" and "II" are confirmed to exist, and they correspond respectively to footprints A and B.

It will be apparent to those skilled in the art that various modifications and variations can be made to the compositions of matter and processes of this invention. In particular, various kinds of screening assays are encompassed that employ human CYP7 regulatory elements or its homologs. Thus, it is intended that the present invention cover the modifications and variations provided they fall within the scope of the appended claims and their equivalents. Lastly, all publications set forth above are expressly incorporated herein in their entirety.

What is claimed is:

1. A HepG2 host cell stably transformed with a construct comprising a human regulatory CYP7 minigene from −371 to the Bgl II site in the middle of intron II (SEQ ID NO:5).

2. The stably transformed HepG2 host cell according to claim 1, wherein said construct further comprises a reporter gene.

3. An assay for detecting an agent that inhibits or stimulates CYP7 expression, comprising the steps of:
    (a) contacting with said agent a host cell according to claim 1 in a medium suitable for CYP7 expression and
    (b) detecting an inhibition or stimulation of CYP7 expression.

4. The stably transformed HepG2 host cell according to claim 2, wherein said reporter gene is luciferase.

5. The method according to claim 3, wherein said agent is a physiological agent endogenous to a human.

6. The method according to claim 3, wherein said agent is a physiological agent exogenous to a human.

7. A method for determining whether an agent stimulates or inhibits CYP7 gene expression comprising the steps of:
    (a) contacting the agent with a transfected cell containing a construct, wherein said construct comprises
        (i) human CYP7 DNA that consists of an isolated regulatory element located within a region from −371 to +24 (SEQ ID NO:5), wherein said element is regulatory with respect to CYP7 expression in the presence of bile acids, and wherein the numbering of said element is measured relative to the transcription start site and
        (ii) heterologous DNA; and
    (b) determining CYP7 gene expression in said cell.

8. The method according to claim 7, wherein said regulatory element comprises nucleotides −65 to −54.

9. The method according to claim 7, wherein said regulatory element is selected from a group of bile acids responsive elements consisting of nucleotides −371 to −221; −173 to −129 and −79 to −34.

10. The method according to claim 7, wherein said heterologous DNA is a reporter gene.

11. The method according to claim 9, wherein said bile acids responsive element consists of nucleotides −371 to −221.

12. The method according to claim 9, wherein said bile acids responsive element consists of nucleotides −173 to −129.

13. The method according to claim 9, wherein said bile acids responsive element consists of nucleotides −79 to −34.

14. A human regulatory CYP7 minigene that can be transformed stably into HepG2 cells comprising a region of the human CYP7 gene from −371 to the Bgl II site in the middle of intron II (SEQ ID NO:5), wherein the numbering of said minigene is measured relative to the transcription start site.

15. A method for determining whether an agent stimulates or inhibits CYP7 gene expression comprising the steps of:
   (a) contacting the agent with a transfected cell containing a construct, wherein said construct comprises
      (i) human CYP7 DNA that consists of an isolated regulatory element located within a region from −371 to −78 (SEQ ID NO:5), wherein said element is regulatory with respect to CYP7 expression in the presence of bile acids, and wherein the numbering of said element is measured relative to the transcription start site, and
      (ii) heterologous DNA; and
   (b) determining CYP7 gene expression in said cell.

16. The method according to claim 15, wherein said bile acids responsive element consists of nucleotides −371 to −221.

17. The method according to claim 15, wherein said bile acids responsive element consists of nucleotides −173 to −129.

18. A HepG2 host cell stably transformed with a construct comprising a human regulatory CYP7 minigene comprising nucleotide sequences from −371 to −78 upstream of nucleotide sequences from −36 to the Bgl II site in the middle of intron II (SEQ ID NO:5), whereby the numbering is relative to the transcription start site of the human CYP7 gene.

19. A HepG2 host cell stably transformed with a construct comprising a human regulatory CYP7 minigene comprising nucleotide sequences from −371 to −221 upstream of nucleotide sequences from −36 to the Bgl II site in the middle of intron II (SEQ ID NO:5), whereby the numbering is relative to the transcription start site of the human CYP7 gene.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CGGGGTACCT GAGATTTGGA TGGGGACACA 30

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TAGGAAGGGA AAGATTAGTG AGCTCGCCAT 30

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TCGGGGTACC TGTGGACTTA GTTCAAGG 28

( 2 ) INFORMATION FOR SEQ ID NO:4:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

```
TACCGCTCGA GTGATTAGAA AGGGAAGGAT                                              30
```

( 2 ) INFORMATION FOR SEQ ID NO:5:

( i ) SEQUENCE CHARACTERISTICS:
        ( A ) LENGTH: 5537 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: join(2300..2380, 3930..4169, 5211..5537)

( x i ) SEQUENCE DESCRIPTION: SEQ ID NO:5:

```
TTTTGGTTA   TCTTTTCAGC   CGTGCCCCAC   TCTACTGGTA   CCAGTTTACT   GTATTAGTCG    60
ATTTTCATGC  TGCTGATAAA   GACATACCTG   AAACTGGACA   ATTTACAAAA   GAAAGAGGTT   120
TATTGGACTT  ACAATTCTAC   ATCACTTGGG   AGGCCTCACA   ATCATGATGG   AAGGAGAAAG   180
GCACATCTCA  CATGGCAGCA   GACAAGAAAA   GAGCTTGTGC   AGGGAAACTC   CTCTTTTTAA   240
AACCATCAGA  TCTCATGAAA   TTTATTCATT   ATCATGACAA   TAGCACAGGA   AGAACTGCA    300
CCCATAATTC  AGTCACCTCC   TACCAGGTTC   CTCCCACAAC   ACGTGAGAAT   TCAAGATGAG   360
ATTTGGATGG  GGACACAGCC   AAACCATGTC   ACACTACCAT   GCCTGACTTC   CTTTCCATTT   420
TTGTATATTT  GCTTGTTCTT   CATTTGCCCG   AGAAGTAACT   CTAAAGGGCT   GTATTATTTG   480
GATATTAGAT  TGGCATTTTA   TCTGACTGGG   ATATCTTGCT   GTGATTGTCC   ATGTATAAGA   540
TCAGCTTTTC  TATAAGCCAT   ATTTTAAAA    AGATATATTA   ATTTTTAAA    AATCCACCTG   600
TCTAAATAAA  TGCACAAAGC   CCCCCAAAAA   CCTAGATTCT   AAGAAAAATC   TATGTACTGC   660
CATACAATGA  TTGATATTAA   TATTTATGGT   GATAAATTAC   ACACAAAAAA   TGTGTGATCT   720
CTGTTTAAAC  AGGCAAAAAC   AAAAAACACA   TGAAATAAAT   CTATGGCATC   TATAGCCAAA   780
ACTGGAAACA  ACCCACATAT   CCATCAATAG   GAAATCAGTT   AAATAAATTA   TAGTACATTT   840
ATCCAATGGA  AGATTAAGCA   CATATTCAAT   ATAATTATTT   ATACACACAT   ATAGATACAC   900
ACATGTATAA  ATATAGAGAA   TACTGTGGGT   GTATGTGTGT   GTGTGTTTAT   ATACATATAT   960
ATACACACAC  AGTACTGTTG   CCTACCTTCT   TTTGTCTTAA   TTCTGTGAAC   TCTCATTCAC  1020
TCTGCTTCAG  TAGGATACCT   CCTTCTTTTT   GGTTCTTAGA   CTCACCAAGT   TGATCCTTGA  1080
CTCAAGACAT  TGCATTTGCT   GCTTCCTCTT   CCTGGAATAT   CCTTCCTTCT   GATATTCACA  1140
TGAGTAGTCT  CTTCTTGTCA   TTCAGATCTC   AAATGTCACA   ATTTCAGAGA   GCCCATCTCT  1200
GATCATCATA  TCTAAAGTTG   TCCTCATTCC   CCCATAGCTT   TCTATACCAT   GTTTTATTTT  1260
TTTCATAACA  TGTATTTTAT   TACTCCTTTC   TCCATTGGAA   TAGAATCTCC   ATTAGATTAG  1320
GAAATCTGCC  TATCTTATTA   ATGCCTGCAA   CTGGAATACT   TTTGAAGAGT   TCTTGGCACG  1380
TAATAAATAC  TCAACTAATA   TTTTTGTGTA   CACAGAAATA   AAGTTTGGAA   GAACAGATGC  1440
CAAATTGTTA  CTAGTGGTTA   CTTCTGAGTA   AAGGAGTAGC   ATGGTAGGTA   AATTATTAAT  1500
AGATGTTCAC  TTTCCACCAA   GATATGTTTT   AGTTAGTCTT   AACTTACTTG   AAATGAAATT  1560
TATTACTTTA  ATAATTAGAA   ACATTGATAA   ACATTTTAGT   CACAAGAATG   ATAGATAAAA  1620
TTTTGATGCT  TCCAATAAGT   TATATTTATC   TAGAGGATGC   ACTTATGTAG   AATACTCTCT  1680
```

-continued

```
TGAGGATGTT AGGTGAGTAA CATGTTACTA TATGTAGTAA AATATCTATG ATTTTATAAA    1740

AGCACTGAAA CATGAAGCAG CAGAAATGTT TTTCCCAGTT CTCTTTCCTC TGAACTTGAT    1800

CACCGTCTCT CTGGCAAAGC ACCTAAATTA ATTCTTCTTT AAAAGTTAAC AAGACCAAAT    1860

TATAAGCTTG ATGAATAACT CATTCTTATC TTTCTTTAAA TGATTATAGT TTATGTATTT    1920

ATTAGCTATG CCCATCTTAA ACAGGTTTAT TTGTTCTTTT TACACATACC AAACTCTTAA    1980

TATTAGCTGT TGTCCCCAGG TCCGAATGTT AAGTCAACAT ATATTGAGA GACCTTCAAC     2040

TTATCAAGTA TTGCAGGTCT CTGATTGCTT TGGAACCACT TCTGATACCT GTGGACTTAG    2100

TTCAAGGCCA GTTACTACCA CTTTTTTTTT TCTAATAGAA TGAACAAATG CTAATTGTT     2160

TGCTTTGTCA ACCAAGCTCA AGTTAATGGA TCTGGATACT ATGTATATAA AAAGCCTAGC    2220

TTGAGTCTCT TTTCAGTGGC ATCCTTCCCT TTCTAATCAG AGATTTCTT  CCTCAGAGAT    2280

TTTGGCCTAG ATTTGCAAA ATG ATG ACC ACA TCT TTG ATT TGG GGG ATT GCT    2332
                     Met Met Thr Thr Ser Leu Ile Trp Gly Ile Ala
                      1               5                    10

ATA GCA GCA TGC TGT TGT CTA TGG CTT ATT CTT GGA ATT AGG AGA AGG     2380
Ile Ala Ala Cys Cys Cys Leu Trp Leu Ile Leu Gly Ile Arg Arg Arg
         15              20                       25

TAAGTAATGT TTATCTTTA AATTGCTCTT TGATTCATCC ATTAATTTT TTTACCTTCA      2440

TTTTTATACA GTAAATTTGG TTTTCTATAC TTACACATAT TAGCATTATC TTCCTTATGT    2500

TTTAAATGAA AAATTTGATT TGAATTTTA AAGTAATATC TTTTTACTA TATCTCACAA      2560

GACATATGAC AGCTTCCCTT TTTAGTATTG GCATATACCG ATGGTAATAT ATAAATGTAT    2620

ATTGGTGTTA AACATAACTG ACAGAAATTG TATAAGGTCT CTATGTACAT TTATATGTGT    2680

ATCTAAAGAG GAAGCCCAGA TTAGTAAGGA TACAAGTAGC AAGTGGGAAT CTACAATGGA    2740

AAGGATTGCT TTCTCTCACA TGGCTTCAAT AGATACTCTT GCTTAAATAA ATGTTCTCTT    2800

TTAAGCTCAT TCTTGTGCAT CGCATAGACT CAGCCTAAGC CTGAACAAGA GCATAGAGCC    2860

TGAGCTGATC ATTCTATTAC TGTTTTTAAA TAAATGTTAA TCAACTGTGG TGAATTGGGA    2920

AAGTTTGCTG AGTGTATGTG ACATCGATTT CATTTATTTA CAACTGGTTC AAGAATGCAA    2980

GAAAAACAAA TACAGTCAGA TCCAGAACCA TAGTTTATTT AACTTCTAAT TGGCTCAAGG    3040

AGTAATTGTG GGGAGGCATA TAGATATTCT CTGCTATGTC AATCTCAAAA AGAGAAAATA    3100

ACCCTAACCA TCTTTCAGCT TTGTAGATTG CTATGTGTTT TCTGCCTTTG CAGTTTCTTT    3160

CAGGCCTGAT AGTTTTTACT TTTAATTAAA CTACTTATCT TCAAACTAAG AAAAGAAAGG    3220

TAATTACTTT ATACTGTATT ATTCTATCAA GAGGTACAGA AGTTTATGTT GGAAAATAAG    3280

TTTACATGTT CTAATAAAAA CATTTTAAAG GAGCACTGAA TTACAATAGA TGATTCCGTC    3340

AGTGTTTATC TTACTCAATT TCATTTTATA ATAAGCTGAT TTCTCACATG AGATTCTTCT    3400

TCTCTGAAAC CATCCTTATA GAATATAATA TAGATATCTT TAAACTAGGA ATATTTTCAA    3460

AACCTCAGTT CTGAAATCCT CCCTTATTCA GTGATCTGTG TCTTTAAAGA AAATAATCAA    3520

AAGAAACATT TTGAGATATT TAGAAAAATG ATGCTTAGCA AAGTGATAAA CACTAGAATG    3580

TAGTTTTGTT TCCGCACTGA CAACAAGAAT CTTGTTGGTC TTGTAAATCC TTTTGCCTGT    3640

ATCACTGGGA AAAGTGATGA GCACATAGTA GACGGGTGCT TGTTGAATGT GTATATGGAC    3700

GGATGCATGA ATGGATGGAT TTAGTAATCC TTTCCACCAA CATATCATGT TACTAGGTTA    3760

ATATAACCTA TTACTGTAGT AAAAGAGCAG GGCCCATCCA ACAAAGAAA TATCTATAAA     3820

CTATAGGGTT TCAAAGTTTG AAGTCAGTGG GAAAAATTTT AAAACCTGAT GTAAGTAAAA    3880

ACCCAAAACT GTAATCATCC ATGTCTATCA TACACTTGTG TCTGACAGG CAA ACG        3935
```

|  |  |  |  |  |  |  |  |  |  |  |  |  |  |  | Gln | Thr |  |
|--|--|--|--|--|--|--|--|--|--|--|--|--|--|--|--|--|--|

```
                                                                Gln  Thr
GGT  GAA  CCA  CCT  CTA  GAG  AAT  GGA  TTA  ATT  CCA  TAC  CTG  GGC  TGT  GCT       3983
Gly  Glu  Pro  Pro  Leu  Glu  Asn  Gly  Leu  Ile  Pro  Tyr  Leu  Gly  Cys  Ala
30                       35                       40                       45

CTG  CAA  TTT  GGT  GCC  AAT  CCT  CTT  GAG  TTC  CTC  AGA  GCA  AAT  CAA  AGG       4031
Leu  Gln  Phe  Gly  Ala  Asn  Pro  Leu  Glu  Phe  Leu  Arg  Ala  Asn  Gln  Arg
                    50                       55                       60

AAA  CAT  GGT  CAT  GTT  TTT  ACC  TGC  AAA  CTA  ATG  GGA  AAA  TAT  GTC  CAT       4079
Lys  His  Gly  His  Val  Phe  Thr  Cys  Lys  Leu  Met  Gly  Lys  Tyr  Val  His
               65                       70                       75

TTC  ATC  ACA  AAT  CCC  TTG  TCA  TAC  CAT  AAG  GTG  TTG  TGC  CAC  GGA  AAA       4127
Phe  Ile  Thr  Asn  Pro  Leu  Ser  Tyr  His  Lys  Val  Leu  Cys  His  Gly  Lys
          80                       85                       90

TAT  TTT  GAT  TGG  AAA  AAA  TTT  CAC  TTT  GCT  ACT  TCT  GCG  AAG                 4169
Tyr  Phe  Asp  Trp  Lys  Lys  Phe  His  Phe  Ala  Thr  Ser  Ala  Lys
     95                      100                      105

GTAAGCAGTT  TTACATTTAT  ATACCATTCT  GTTTGTCTTC  TACCTTTTTA  TGTGCTTGTC              4229
TATTTAGAAA  TTTTGATGTA  CTTAGATTTT  ATGATAAAGG  TGTTGAAGAG  AGTTATCCTT              4289
ATGTGGAGAT  TCTTAGAAAC  ATAAATAAAT  TATACGTAGC  TTCTTAGTAA  TAATCATTTA              4349
GAAAGTCAAA  ATAGGTATAG  ATTTCCGTCA  TTTGCTTTGC  ACGAGCTAAT  GAGGGTGAAA              4409
TACAGATTAA  ATGCTCTACT  GAGACAGGTG  GCACTGTACG  AATAAGATAG  ATTAAAATTC              4469
ATCACATCAG  CAATGTCTAT  GCAGAGCGAA  GTGACGGAAA  CCTAACATTC  AGCAGTTGTC              4529
TCACCACACT  TGTGCCACAC  AGTGTTTCAT  TTTGATAAGG  AATTGGCAAG  ATATTTTAAC              4589
ATCATTTAGA  TGTAATAAAA  GAAGATCTGT  TACTGAGAAA  AAAAACCAAT  AACTACTTAC              4649
TTACTGCAAA  TAAATATTAG  CTTTGGTCTT  TGTGACTAAG  TAGCTTAAAG  TTTGGTTAAA              4709
ATACATCTAC  AGCTGGACAC  AATGGAACAC  ACCTGTAGTC  CCTGCTATTT  GAGAGGCTGA              4769
GGCAGGAGGA  TCGCTTGAGT  CCAGGAGTTT  GAGGCTGCAG  TGAGCTATCA  TTGTGTCACT              4829
GCACTCCAGC  CTGGGTGACA  ATGTGAGACC  CCATCTCTAA  AGAAAAAGA   AAAAGAAATC              4889
TACAAATAAT  ATAAAGATA   ACTAATGATT  TTAAAACATT  ATCAATTAGT  TTATGTGCAA              4949
TAGCTGTAAA  TAAGTGCAGT  AGCATAAGAA  ATAAGACATA  GATGACTTGA  GTGATCCAGG              5009
GGAGTGCCAC  TGAAGTTGGC  TTTAAAGGAA  AGGTACAGTT  TGGTCATTTA  TTTGTAAAGT              5069
GCTATGAACT  TGTACAAGGG  AAAGCCAATT  TCCCGTGTTT  ACCAAGTAAG  GAACTATGAA              5129
AGTATCTAAT  CCGTTTTTCA  GTCATTACT   ATGACTAGGT  CAGGTTAAC   TTCTTTTTCT              5189
GCATGTTTTA  TTTGCTATCA  G  GCA  TTT  GGG  CAC  AGA  AGC  ATT  GAC  CCG  ATG         5240
                          Ala  Phe  Gly  His  Arg  Ser  Ile  Asp  Pro  Met
                                         110                      115

GAT  GGA  AAT  ACC  ACT  GAA  AAC  ATA  AAC  GAC  ACT  TTC  ATC  AAA  ACC  CTG      5288
Asp  Gly  Asn  Thr  Thr  Glu  Asn  Ile  Asn  Asp  Thr  Phe  Ile  Lys  Thr  Leu
               120                      125                      130

CAG  GGC  CAT  GCC  TTG  AAT  TCC  CTC  ACG  GAA  AGC  ATG  ATG  GAA  AAC  CTC      5336
Gln  Gly  His  Ala  Leu  Asn  Ser  Leu  Thr  Glu  Ser  Met  Met  Glu  Asn  Leu
     135                      140                      145

CAA  CGT  ATC  ATG  AGA  CCT  CCA  GTC  TCC  TCT  AAC  TCA  AAG  ACC  GCT  GCC      5384
Gln  Arg  Ile  Met  Arg  Pro  Pro  Val  Ser  Ser  Asn  Ser  Lys  Thr  Ala  Ala
150                      155                      160                      165

TGG  GTG  ACA  GAA  GGG  ATG  TAT  TCT  TTC  TGC  TAC  CGA  GTG  ATG  TTT  GAA      5432
Trp  Val  Thr  Glu  Gly  Met  Tyr  Ser  Phe  Cys  Tyr  Arg  Val  Met  Phe  Glu
                         170                      175                      180

GCT  GGG  TAT  TTA  ACT  ATC  TTT  GGC  AGA  GAT  CTT  ACA  AGG  CGG  GAC  ACA      5480
Ala  Gly  Tyr  Leu  Thr  Ile  Phe  Gly  Arg  Asp  Leu  Thr  Arg  Arg  Asp  Thr
               185                      190                      195
```

| CAG | AAA | GCA | CAT | ATT | CTA | AAC | AAT | CTT | GAC | AAC | TTC | AAG | CAA | TTC | GAC | 5528 |
| Gln | Lys | Ala | His | Ile | Leu | Asn | Asn | Leu | Asp | Asn | Phe | Lys | Gln | Phe | Asp | |
| | | 200 | | | | | 205 | | | | | 210 | | | | |

| AAA | GTC | TTT | | | | | | | | | | | | | | 5537 |
| Lys | Val | Phe | | | | | | | | | | | | | | |
| | | 215 | | | | | | | | | | | | | | |

(2) INFORMATION FOR SEQ ID NO:6:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO:6:

| Met | Met | Thr | Thr | Ser | Leu | Ile | Trp | Gly | Ile | Ala | Ile | Ala | Ala | Cys | Cys |
| 1 | | | | 5 | | | | | 10 | | | | | 15 | |
| Cys | Leu | Trp | Leu | Ile | Leu | Gly | Ile | Arg | Arg | Arg | Gln | Thr | Gly | Glu | Pro |
| | | | | 20 | | | | | 25 | | | | | 30 | |
| Pro | Leu | Glu | Asn | Gly | Leu | Ile | Pro | Tyr | Leu | Gly | Cys | Ala | Leu | Gln | Phe |
| | | | | 35 | | | | | 40 | | | | | 45 | |
| Gly | Ala | Asn | Pro | Leu | Glu | Phe | Leu | Arg | Ala | Asn | Gln | Arg | Lys | His | Gly |
| | | | | 50 | | | | | 55 | | | | | 60 | |
| His | Val | Phe | Thr | Cys | Lys | Leu | Met | Gly | Lys | Tyr | Val | His | Phe | Ile | Thr |
| 65 | | | | | 70 | | | | | 75 | | | | | 80 |
| Asn | Pro | Leu | Ser | Tyr | His | Lys | Val | Leu | Cys | His | Gly | Lys | Tyr | Phe | Asp |
| | | | | 85 | | | | | 90 | | | | | 95 | |
| Trp | Lys | Lys | Phe | His | Phe | Ala | Thr | Ser | Ala | Lys | Ala | Phe | Gly | His | Arg |
| | | | | 100 | | | | | 105 | | | | | 110 | |
| Ser | Ile | Asp | Pro | Met | Asp | Gly | Asn | Thr | Thr | Glu | Asn | Ile | Asn | Asp | Thr |
| | | | | 115 | | | | | 120 | | | | | 125 | |
| Phe | Ile | Lys | Thr | Leu | Gln | Gly | His | Ala | Leu | Asn | Ser | Leu | Thr | Glu | Ser |
| | | | | 130 | | | | | 135 | | | | | 140 | |
| Met | Met | Glu | Asn | Leu | Gln | Arg | Ile | Met | Arg | Pro | Pro | Val | Ser | Ser | Asn |
| 145 | | | | | 150 | | | | | 155 | | | | | 160 |
| Ser | Lys | Thr | Ala | Ala | Trp | Val | Thr | Glu | Gly | Met | Tyr | Ser | Phe | Cys | Tyr |
| | | | | 165 | | | | | 170 | | | | | 175 | |
| Arg | Val | Met | Phe | Glu | Ala | Gly | Tyr | Leu | Thr | Ile | Phe | Gly | Arg | Asp | Leu |
| | | | | 180 | | | | | 185 | | | | | 190 | |
| Thr | Arg | Arg | Asp | Thr | Gln | Lys | Ala | His | Ile | Leu | Asn | Asn | Leu | Asp | Asn |
| | | | | 195 | | | | | 200 | | | | | 205 | |
| Phe | Lys | Gln | Phe | Asp | Lys | Val | Phe | | | | | | | | |
| | | | | 210 | | | 215 | | | | | | | | |

(2) INFORMATION FOR SEQ ID NO:7:

(i) SEQUENCE CHARACTERISTICS:
        (A) LENGTH: 7997 base pairs
        (B) TYPE: nucleic acid
        (C) STRANDEDNESS: single
        (D) TOPOLOGY: linear (xi) SEQUENCE DESCRIPTION: SEQ ID NO:7:

| GAGCTCTACC | CTTGCTCTGC | TATTGTACTT | TTTAATACAC | AGTTCAATCA | AATGTGCCAC | 60 |
| CAGAATATGC | ATGCTAACAG | CTGTAGTGGT | TGATTTTTCT | TTCTACTCTT | CTGTGTGTAA | 120 |
| GACCCCATGT | TTTATCAATT | ATTTTTTAAT | GATTTCTTTC | TTCATGCATA | TGTGTGGTTG | 180 |
| TCAGTGTGAG | TCTGTGTGTA | CAGCAGGTGC | ACAGGTATCC | ACAGAGGCCA | GAGGTTCCCT | 240 |

```
GTAACTAGAA TTACAGGCAC TTGTGAACTT TCCTGTATGG GTGCTGGGAA GCAATCTGAG      300
GTCTTCTGCA AGGGATCTTA ACCACTGACT TTCTAGCCTG CTTTGCCCAT TTCTATTTAT      360
GATGACTGGA AACTGGGCTT AGGCCTTATA TTCTCTGAGG CCAAAATCAA GTTCTTCCAA      420
ACTGCAGGAT TTATGGTCTT CTATAGTATC CCACAGAAAT GGAAAGAAA GTGACCCATT       480
AGAGCAGTAT TAGAGTCGAA ATAAACTCAA CTTGGTATGC CAGGACTTTG DACAATAATA      540
ACCCTGTCTT TTCAGGGCAT CTATCTGTAC TGCTGCAATA GAAACTCCAC AGGTCAGGGT      600
CACAGCTGTT GTGTTTTACA CAGTGTCCCC AGGATTAGTT CAGTGCCCAC CATGCAATAG      660
GTGTCATGGT GTGTGTGTGT GTGTGTGTGC GTGTGTCGTG CTTGTGTGCA TGTGTGTGAG      720
ACACACACAC AGAGAGATAC AAAGACAGAA ACAGAAAATT AATAAATTT TACCAACTAA       780
AATAGGGAAT TAAAGAAAAG GAGGAGAAAA AGTTGGGCAT TCAACACCAT AAAGTCCCAG      840
TACTATGCTA AGAACACCCA GCTGTCCTCA CACCCGGGCA TGAAACTTCA TGCACTGTTC      900
ATCAGAAAAT CGTTTACACA CATCCCCTTG CAGTCTACTT GTAGTTTTAA CAACTTCAGA      960
GAGCACTAGC ATTTCCAGCC CCAGGTTAGA AGCTTTGGTA GATGCTGTTT GCGAGCACAG     1020
GATAGCAGCA AGAAGTGGAC TTGTTAGAAG GAAAGCCAAT GCCTATGTAA CAACGAAAAC     1080
TAAGTATGAA TCTCGAATCT CCACTCTCGT GTGTCTGTGT CTCCATATAC GTGCTTGGGT     1140
GCCTGACATG GCAAGGTGTT ACAAGTAAGG GAGGAACAAG AAAAGGACAG GGTAGTGGAC     1200
ATCAGGATGA ATGCCAGCCA GGGCGACTGG AGAGAGTCTA CGCTGCTCTG AAGGTGGGTG     1260
AAGAAGACCT CAGGAAGCTT TCTGAGGCTC CGAGAGTGCT TTTCCCTTCC CATGTTGAAA     1320
CATCCTTATT TGCAGAGAAT TCCAGGTTCA TGGAATTTG TAAAGAGAAT ACTAAGAGGC      1380
CACCTGTGGC TTCTCCTATT TTTGTCTGCT GTCATTTATG GGACAGGGTT AGAGACCTGG     1440
CTTGCTTGGC TATGAGGCTG TTGCTTCCTC GGTTACTCTG CTGTGGTTGG ATGCATTAGG     1500
GTTAGGCCCC TCAAGAGCCA TGTGTCATTT TATAAAAGCA ATATAAATAT ACTTAAGGTG     1560
CACAAAGCAT TAGGAGGTCT GAGATAATAG ATTCTGAGAA AATCTATCCT GCTGTGTAGC    1620
AACTGATGTT TATGATTATA GTCCCAGACC ACACGATAAA GGATCTGTGG ACTCTGTTTA    1680
GGGAGGTCAA AAAACTATTG CAAATGGAGT CTATAGAGAA AACTAGACAG GACTCAATGC    1740
TCACCAATCG AGAATTAGTT GATGAGCTGG GGTAGTGACT TAGTGGATAA GAACACGGTC    1800
CTTTCAGAGG TCCTGAGTTA AATCCCCAGC AAACACATGG TGGCTCATAA CCATCTATAT    1860
TGTGATTTGA TGCCCTCTTC TGGCATGCAG GTGTACATGC AGACTCGTAT ACATAAAATA    1920
AATAAATCTT GAAAAAATGA ATACGTTGAA TAAGTGTCCC CTCGGATAAC TTTCTGCAGA    1980
ATTTTAAGCA CATGTCAATG GTAATAACAC ACACACACAC ACACACACAC ACACACACAC    2040
ACACACATAC ACACACCATA CAGATATGTA TCTAGAGACA TACACATGTA CATTTTATCT    2100
CTTTTATTTT CTTCTCCCCT CTTTGACATC AAGGAATAGA ATGCACTCAC TGTGGCCTAG    2160
TGCCACACTC TACCTATTTC TTTGGCTTTA CTTTGTGCTA GGTGACCCGA AAGGTTTAAA    2220
TATCAAAAAT GCTAATGGCT CGACATTTAC ATCCCCAATT TCTCCTTTCT CCTTACCTCA    2280
GACTCTTACA TTCAGTTGAC AATTTGACAT CGTCTCCTGG ATTTTCAAAT GTTCAGCACA    2340
CTGTACTGAT GTACTGCCTT CCAAGGCAAC CGGCACGATC CTCTCCCCAC TCCCAAGCAT    2400
CCCTCCATGA GCCAGTGTTT GCTTATCTTC TTGACTCTTG TTTTAACCCA ACTCCTCCCC    2460
TATTCACTCT GCTCTAATTC ATTCATTCTA TATTTTCGCA CATCAGGCTC ATCCTTTGCT    2520
CAGGAACTTC ACTTTTGCTT TCCGGTCTCC TGGAAATGTG TTTTCTTGGC TATTCCATCT    2580
CAAGACCATC TTTTCAGAAA AGCTTTTCCT ATCAACATAT TTAAAGCCCT CTTCATCCCC    2640
```

```
CAGTAGCTCT GGACACCTCA TTTTATGGAT ACACAACACA TATTTGCCAC CTGTCTCCCC    2700
ATTAAAATAT AATCTTCAGT AGAGAAACTC CATATCTTGT TAATACCTGA AACAAGAATA    2760
TCTTCAAAGA GTTCCTGGGA CATAAAAACG CTCAATTAAT ATTTATGTTA AACAGGGATC    2820
TGGGGTATAT CACAGAGGTA GAGGGCTTAC CTAGGAGGAG TTGGGCCATG GGTTCAACTT    2880
CCAGCACAGA ATGAAAGATT ATGTTAAATA AGTTGGGAA GGATGTATGC CAGTCTATGA     2940
GTAGTATAGG AGGTAAATTA TGAATTCATA TTTACTTTTC GGACAAGAAG TGTTGTAGTC    3000
TTTATTTGAA ATAAATACA TCTTAATTAC CAATAACAAT GGTAAGGAG TGAATTCTCA      3060
AGCTGTGGCT TCCTGGTAGA TGAGTCCTGG GAGGTTTTCT ATTTCGATGA TGGTAGATAG    3120
GTAACCTGTC ATATACCACA TGAAATACCT GTGGCTTTGT AAACACACCG AGCAGTCAAG    3180
CAGGAGAATA GTTCCATACA GTTCGCGTCC CTTAGGATTG GTTTCGGGAT ACTTCTGGAG    3240
GTTCATTTAA ATAATTTTCC CCGAAGTACA TTATGGGCAG CCAGTGTTGT GATGGGAAGC    3300
TTCTGCCTGT TTTGCTTTGC GTCGTGCTCC ACACCTTTGA CAGATGTGCT CTCATCTGTT    3360
TACTTCTTTT TCTACACACA GAGCACAGCA TTAGCTGCTG TCCCGGCTTT GGATGTTATG    3420
TCAGCACATG AGGGACAGAC CTTCAGCTTA TCGAGTATTG CAGCTCTCTG TTTGTTCTGG    3480
AGCCTCTTCT GAGACTATGG ACTTAGTTCA AGGCCGGGTA ATGCTATTTT TTTCTTCTTT    3540
TTTCTAGTAG GAGGACAAAT AGTGTTTGCT TTGGTCACTC AAGTTCAAGT TATTGGATCA    3600
TGGTCCTGTG CACATATAAA GTCTAGTCAG ACCCACTGTT TCGGGACAGC CTTGCTTTGC    3660
TAGGCAAAGA GTCTCCCCTT TGGAAATTTT CCTGCTTTTG CAAAATGATG ACTATTTCTT    3720
TGATTTGGGG AATTGCCGTG TTGGTGAGCT GTTGCATATG GTTTATTGTT GGAATAAGGA    3780
GAAGGTATGG AAAGATTTTT AAAAATTTGT CTTTTAGCTT ATTTCTAGTA TTCATTGCCT    3840
TCACTATTAT GTAGTGCAAA AAATACTAAT GCATTAATAT TTTTAAATTT AAAATTTAAA    3900
GACGTACTTC TTTGACTAAA TCTAGTAAGA TGTAGAGAGT CCCCCTTGGA ACATTCACAT    3960
ATGCCACTGG TAATGCAGAT CTTGTGAAAT ATAACTAAAG AAATCACAAG TCATCGATGT    4020
AAGTTTGTGT CTGCATGGGC GGAACAAACC TAAGCTAAGA AGAGTAGTAT TTGGGAGGGA    4080
TCTTTCTGTG ACATGAACTG AATAGACGCA CTGCCTCAGC AAACACACAT TCATTTGAAT    4140
TTTCCTCAGA CTCAGTCTAA GCCTGGTGAG AGCACCAAGT GTGAGTCTGT CTGCCACTAA    4200
CGTTTCCTTC CAGTGGTAAT CAGCTGTGTG GCTGTGAAAC CTTGGCGCCT GCACATGACA    4260
GCCATTTGAA TAGTTCAAAG AACATTTAGG GACAGGATAT TAAGATATTT TCTGTGATGT    4320
CAACATCAAA ATAGGAGAAT GCCCCTGGCA TTATCTTCAG AGAGGTAGAC TACTGTGCGT    4380
TGTCTTACTT TAAAGAAATT TCTTTGCCCC TTTGGCTATT TTAATTCAAA CCTGAAAGTT    4440
TTCAGTTTTA ATTAAACTGT TGATTTTCAT GCTAGGAAAG GAAATATCAA TTATACTTAA    4500
TTGTTCTTAC AAGAAATAAA ATCATTTATG TCGGGAGATA AATAAGCTCA TAATTTTAAT    4560
AAAACATTTA AGAGAGAGAA AAAGAGTAGT GGATTATAGT TCATTGTCTG TCAATGTTTA    4620
CCTGACCCAG TTTCATTTTA TAATTATCTA ATTTTTCAAA TGAGATTCCT GTTCTTTCCA    4680
AATATCATTG CAGAATACTA ACATTCTTTT TTTCAGAGTT GAGAATCAAA TGGAGGGTTT    4740
TTTCATCCTG GCACAAGCTC CGCTCTTCAG TAACACCTCC AGCCCTCAGA ATGCCAATAT    4800
TTTAAATTAT GTAGGTTGTT AAAACTTTAG TGCTGGGGCT GGGGATTTAG CTCAGTGGTA    4860
GAGCACTTGC CTAGCAAGCG CAAGGCCCTG GGTTCGGTCC CCAGCTCTGA AAAAAGAAA    4920
AAGAAAAAAA AAAACTTTAG TGCTGTAGCC CTTTCTGTTA TTTGATGTTT CACATCTGTT    4980
AAAAAACAAA ACAAAACAAA AAAAACAAGC AAATGGAACA TTTTAGGCAT TCTTTGGGGG    5040
```

```
AAATGATTCT   TAGAGCAAGT   CTAATCATTA   GGTGATAGTT   TCATTTTTAC   ACCAAGAACA   5100
AGAATCTTGT   TGGCTGTGTT   AACACTTTAA   GCCCTGTTGT   AGGGAAAAAG   CAATCAGACA   5160
CAGGCACAGA   AAAGAATTTG   GATGAGTACT   TGATGATGTA   TGTATATATG   GTGAATAGAC   5220
TGATGGGTGG   GCTGCTGGCT   GGGTTGGTAA   GTGGGTAGAT   TTTTTTTTAA   AGATTTATTC   5280
ATTTATTATA   TATCAGTACA   CTGTAGCTAT   CTTCAGATAC   ACCAGAAGGG   CATCGGATCT   5340
CTTTACAGAT   GGTTGTGAGC   CACCATGTTT   TCCTAACCTC   TCAAGTCTCT   GTCTTCCAGG   5400
AAAGCTGGTG   AACCTCCTTT   GGAGAACGGG   TTGATTCCGT   ACCTGGGCTG   TGCTCTGAAA   5460
TTTGGATCTA   ATCCTCTTGA   GTTCCTAAGA   GCTAATCAAA   GGAAGCATGG   TCACGTTTTT   5520
ACCTGCAAAC   TGATGGGGAA   ATATGTCCAT   TTCATCACAA   ACTCCCTGTC   ATACCACAAA   5580
GTCTTATGTC   ATGGAAAATA   TTTTGACTGG   AAAAAATTTC   ATTACACTAC   TTCTGCGAAG   5640
GTAATTAATT   CGTTATACAG   ATTCTGTTTG   TTTCCTGGTC   TGTTGATGTA   TTAGTGTATT   5700
TAGTTGTTCC   AATTTTGTTA   GGTTGCAGAA   TAGAGGTAAC   ATAAAATCAG   GGCGTTTCTT   5760
AGTAATAAGC   ATTAGACATT   TAAGGCAGAT   GTAAACCTGT   CATTGATGAT   TCCGGAGACA   5820
GAGGACACTG   CAGGAATCAG   GAAGGTACAG   ATTCATAGCA   CCACTCGTCC   CTTAACAACA   5880
CCCTGAGCAG   GGTGTTGGCA   CTCTTAGCCT   TCAGTCCTTG   TACACGTT    TCATTCCTAA   5940
GATATAGGCT   GTATATTTAA   ACACGATTTG   GAAGCCATCA   AGAATCTGTT   CTAGAGAAAA   6000
CAGCATTTAA   TGATCTTTTG   CAAGAAAATA   TCAGTTATAG   TCTCTGTCAT   TAAGTACATT   6060
GTAATCTGGT   TAAAGAGTAT   CTACTAAGAA   AGTAAAGGCA   GATTAGAACA   ATACCAATGG   6120
ATGATGGGCC   ATCCAGAGAA   ATCCTACTGT   AAATGCTGGG   ATTTAAACTT   GACCCCAAGG   6180
AAGAGTATGA   CTTGATTCTA   CCTTTGGAAT   GTGCTGTAAA   ATCATATTAG   GGAAGGTTCC   6240
AGACAGAGAA   GTGGGATGTA   TTTAATCTAT   CTTCCAGCCC   ACTCTCTAAC   ACTAGCTAGC   6300
TTTGGGCTTT   AGACCCTCCC   CATTTCATGG   ATTCTATTTT   CTACCAGGCA   TTTGGACACA   6360
GAAGCATTGA   CCCAAATGAT   GGAAATACCA   CGGAAAATAT   AAACAACACT   TTTACCAAAA   6420
CCCTCCAGGG   AGATGCTCTG   TGTTCACTTT   CTGAAGCCAT   GATGCAAAAC   CTCCAATCTG   6480
TCATGAGACC   TCCTGGCCTT   CCTAAATCAA   AGAGCAATGC   CTGGGTCACG   GAAGGGATGT   6540
ATGCCTTCTG   TTACCGAGTG   ATGTTTGAAG   CCGGCTATCT   AACACTGTTT   GGCAGAGATA   6600
TTTCAAAGAC   AGACACACAA   AAAGCACTTA   TTCTAAACAA   CCTTGACAAC   TTCAAACAAT   6660
TTGACCAAGT   CTTTCCGGCA   CTGGTGGCAG   GCCTTCCTAT   TCACTTGTTC   AAGACCGCAC   6720
ATAAAGCTCG   GGAAAAGCTG   GCTGAGGGAT   TGAAGCACAA   GAACCTGTGT   GTGAGGGACC   6780
AGGTCTCTGA   ACTGATCCGT   CTACGTATGT   TTCTCAATGA   CACGCTCTCC   ACCTTTGACG   6840
ACATGGAGAA   GGCCAAGACG   CACCTCGCTA   TCCTCTGGGC   ATCTCAAGCA   AACACCATTC   6900
CTGCAACCTT   TTGGAGCTTA   TTTCAAATGA   TCAGGTAACT   TTCCAGTGAC   AGAAATTGCA   6960
TTTTAAACTC   AAAACCCAAA   AAGACTTATA   GAGCTTTCTG   TGCTATCAAC   AAAGAAAGTA   7020
ATACTCAATG   TCCGTGTTTA   GCATGTGCGT   AACAGAAGCA   GCAATTTTTA   GGTGCACAGT   7080
CCCATCGAAA   GGGATGTCCC   AGAAGCCACA   GAACTCAGAC   AGGTTGGTGC   TCCATTAGTA   7140
CAGGTTCCCT   GGCCTAGTCT   TGCTCCTCAC   CCGATATGTT   CCTCTTAATA   TCAAATTAAA   7200
TCCCCGAGTG   CAGTCGTCAC   CACCATATAA   ACATTTGAAA   TGATGACTGA   CTTGCAGGTG   7260
TGATAAGAGC   AGTGACCATA   CCTTACTAAT   TCACTGGAAT   TCATAGGCAA   AGTAACACCA   7320
TCGATTTTGT   ATTCATATAG   GAGCTGCAGC   CATATTTTAA   ATAGCACAAC   TACTTGTTAG   7380
TCAAGCATTC   TGAGGCTCAC   TGTAATCAGG   TAAAGTAGGT   TTAACTCAGC   GTCCTACCAG   7440
```

-continued

| | | | | | | |
|---|---|---|---|---|---|---|
| TTCCAGGCAT | TGAAATGGAA | TATCCTTTAT | CCCACCCATT | CAAAACGTAA | TATATAAATG | 7500 |
| GAAGGCACAG | TTTTGAAGGC | CATGGTATGA | TTAGGGAAT | TTACTCTCAT | GGTCCAATCC | 7560 |
| CTTGTAATTG | TATGCTAGGT | GACATATCCT | TCTGACTTAC | TATGTTCATC | GTATATTCAA | 7620 |
| TCCTTAGTTT | ATAGAGACTG | ACCAAAGCTC | TGCTTTTGCA | TAGCAAAGCT | CCTTTTAATG | 7680 |
| CCCATTCCTA | AACTCAAGGA | CACGAATCCA | GTTCAGTGCC | CTTTTGCATA | CTCCCTGGCA | 7740 |
| GACTCCCGTT | GCCATACATC | CTCCCTCGCT | CGATTCCCAT | GACCTCGCCC | TTGCACACCC | 7800 |
| TGGTACTAGG | ACCTCTCCTG | GCGATACTTC | CTACTACCTA | TGCCACCTCA | TTAAAGGAA | 7860 |
| GGGATAATTG | CTATTTACTT | GCAGTTCTCT | GAATGAGGAC | ATTTTCCCCA | TACGGCTCTT | 7920 |
| TCCACAGGAG | TCCTGAAGCA | ATGAAAGCAG | CCTCTGAAGA | AGTGAGTGGA | GCTTTACAGA | 7980 |
| GTGCTGGCCA | AGAGCTC | | | | | 7997 |

( 2 ) INFORMATION FOR SEQ ID NO:8:

( i ) SEQUENCE CHARACTERISTICS:
        ( A ) LENGTH: 453 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

| | | | | | | |
|---|---|---|---|---|---|---|
| ATACTTCTGG | AGGTTCATTT | AAATAATTTT | CCCCGAAGGG | TAACATTATG | GGCAGCCAGT | 60 |
| GTTGTGATGG | GAAGCTTCTG | CCTGTTTTGC | TTTGCGTCGT | GCTCCACACC | TTTGACAGAT | 120 |
| CTGCTCATCT | GTTTACTTCT | TTTTCTACAC | ACAGAGCACA | GCATTAGCTG | CTGTCCCGGC | 180 |
| TTTGGATGTT | ATGTCAGCAC | ATGAGGGACA | GACCTTCAGC | TTATCGAGTA | TTGCAGCTCT | 240 |
| CTGTTTGTTC | TGGAGCCTCT | TCTGAGACTA | TGGACTTAGT | TCAAGGCCGG | GTAATGCTAT | 300 |
| TTTTTTCTTC | TTTTTTCTAG | TAGGAGGACA | AATAGTGTTT | GCTTTGGTCA | CTCAAGTTCA | 360 |
| AGTTATTGGA | TCATGGTCCT | GTGCACATAT | AAAGTCTAGT | CAGACCCACT | GTTTCGGGAC | 420 |
| AGCCTTGCTT | TGCTAGGCAA | AGAGTCTCCC | CTC | | | 453 |